(12) United States Patent
Saso et al.

(10) Patent No.: US 7,470,803 B2
(45) Date of Patent: Dec. 30, 2008

(54) COMPOUNDS FOR FORMING PHOTOCONVERTIBLE ORGANIC THIN FILM AND ORGANIC THIN FILM FORMED BODY

(75) Inventors: Haruo Saso, Ichihara (JP); Yoshitaka Fujita, Ichihara (JP); Toshiaki Takahashi, Ichihara (JP)

(73) Assignee: Nippon Soda Co., Ltd., Tokyo (JP)

( * ) Notice: Subject to any disclaimer, the term of this patent is extended or adjusted under 35 U.S.C. 154(b) by 302 days.

(21) Appl. No.: 10/543,823

(22) PCT Filed: Jan. 30, 2004

(86) PCT No.: PCT/JP2004/000884

§ 371 (c)(1),
(2), (4) Date: Jul. 28, 2005

(87) PCT Pub. No.: WO2004/067540

PCT Pub. Date: Aug. 12, 2004

(65) Prior Publication Data

US 2006/0138400 A1 Jun. 29, 2006

(30) Foreign Application Priority Data

Jan. 31, 2003 (JP) ............................... 2003-023457

(51) Int. Cl.
*H01L 29/08* (2006.01)
*C07F 7/04* (2006.01)
(52) U.S. Cl. ......................... 556/427; 257/40
(58) Field of Classification Search .................. None
See application file for complete search history.

(56) References Cited

U.S. PATENT DOCUMENTS

| | | | |
|---|---|---|---|
| 4,665,179 A | 5/1987 | Wunderlich et al. | |
| 4,727,015 A * | 2/1988 | Moore | 430/377 |
| 5,017,579 A | 5/1991 | Gubin et al. | |
| 6,338,931 B1 | 1/2002 | Maeda et al. | |

FOREIGN PATENT DOCUMENTS

| | | |
|---|---|---|
| JP | 60-235840 | 11/1985 |
| JP | 61221258 | 10/1986 |
| JP | 07-048251 | 2/1995 |
| JP | 07-297100 | 11/1995 |
| JP | 2001-109103 | 4/2001 |
| JP | 2001-129474 | 5/2001 |
| JP | 2001-215719 | 8/2001 |
| JP | 2002-023356 | 1/2002 |
| JP | 2002-080481 | 3/2002 |
| JP | 2003-301059 | 10/2003 |
| JP | 2004001354 | 1/2004 |

OTHER PUBLICATIONS

Knusli (Chem Abstract 1950: 22496, 1950; Abstract of "Gazzetta Chemica Italiana 1949, 79-621-620").*

Korean Office Action for Application No. 2005-7013887, dated Sep. 28, 2006.

Dulcey, Charles S. et al., "Deep UV Photochemistry of Chemisorbed Monlayers: Patterned Coplanar Molecular Assemblies," *Science*, vol. 252:551-554 (Apr. 1991).

Dulcey, Charles S. et al., Photochemistry and Patterning of Self-Assembled Monolayer Films Containing Aromatic Hydrocarbon Functional Groups, *Langmuir*, vol. 12:1638-1650 (1996).

Lee, Inhyung et al., "Surface-Induced Photoreaction of Benzyl Phenyl Sulfide Monolayers on Silver and Its Application to Preparing Patterned Binary Monolayers," *Langmuir*, vol. 16:9963-9967 (2000).

Toyoda, Naoyuki et al., "Synthesis and properties of silylating reagents having a benzyl phenyl sulfone moity (2)—Comparison of photosensitivity with a phenethylsilane monolayer," Collection of papers scheduled for submission at the 79th Spring Meeting of the Chemical Society of Japan, 2 C6-46 (2001).

Yamaguchi, Kazuo et al., "Novel Silane Coupling Agents Containing a Photolabile 2-Nitrobenzyl Ester for Introduction of a Carboxy Group on the Surface of Silica Gel," *Chemistry Letters*, pp. 228-229 (2000).

Toyoda, Naoyuki et al., "Synthesis of properties of an organosilane having a benzyl phenyl sulfone moiety (1)—Photocontrol of wettability of silica surface," *Chemical Resources Laboratory, Tokyo Institute of Technology*, 2PB 224, (2001).

Tillman, Nolan et al., "Incorporation of Phenoxy Groups in Self-Assembled Monolayers of Trichlorosilane Derivatives: Effects on Film Thickness, Wettability, and Molecular Orientation," *J. Am. Chem. Soc.*, vol. 110:6163-6144 (1988).

English translation of Japanese Office Action issued in JP 2005-504759 dated Jun. 10, 2008.

* cited by examiner

*Primary Examiner*—Samuel A Barts
(74) *Attorney, Agent, or Firm*—Darby & Darby P.C.

(57) ABSTRACT

The present invention relates to a compound which is flexibly amenable to the alteration, without impairing its photosensitivity, of its structural moiety which affects film forming ability and the resulting surface properties, the compound being capable of undergoing surface alteration by irradiation with relatively low energy wavelength, and of forming an organic thin film on a substrate with good reproducibility, and an organic thin film formed body, the compound being represented by formula (1). (In the formula, X represents a heteroatom-containing functional group capable of interacting with a surface of a metal or a metallic oxide, R represents a C1 to C20 alkyl group, a C1 to C20 alkoxy group, an aryl group, or a C1 to C20 alkoxycarbonyl group; n represents an integer of 1 to 30, and m represents an integer of 0 to 5; G1 represents a single bond or a bivalent hydrocarbon radical having carbon atoms of 1 to 3; Ar represents an aromatic group which may have a substituent; G2 represents O, S, or Nr.)

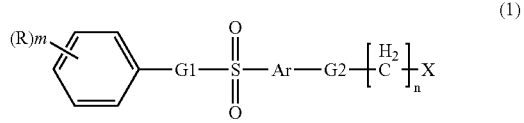

(1)

4 Claims, No Drawings

COMPOUNDS FOR FORMING PHOTOCONVERTIBLE ORGANIC THIN FILM AND ORGANIC THIN FILM FORMED BODY

RELATED APPLICATIONS

This application is a 35 U.S.C. 371 national stage filing of International Application No. PCT/JP2004/000884, filed Jan. 30, 2004, which claims priority to Japanese Patent Application No. 2003-023457 filed on Jan. 31, 2003 in Japan. The contents of the aforementioned applications are hereby incorporated by reference.

TECHNICAL FIELD

The present invention relates to a compound which can form an organic thin film amenable to the selective alteration of its surface properties by light irradiation, in order to simplify patterning process in electronics products and to improve the reliability thereof, a compound which can use the corresponding physical change as a memory element, a production method thereof, and an organic thin film formed body prepared by forming the organic thin film containing the compound.

BACKGROUND ART

Compounds which form an organic thin film of which surface physical properties can be selectively changed by light irradiation to simplify a patterning process, although the process is generally complicated, in producing electronics products, and to improve the reliability thereof are known. With regard to a self-organized organic thin film of which surface physical properties can be changed by light irradiation, it is known in the prior art that the hydrophilic surface is formed following the cleavage of a silicon-carbon bond at a part irradiated with a laser beam at 193 nm on a thin film formed on a substrate by self-organization of an arylsilane compound or an aralkylsilane compound (Non-Patent Literatures 1 and 2).

It is also known that the surface physical properties of the predetermined part of self-organized benzyl phenyl sulfide film can be changed by photo-irradiation to make only unirradiated organic molecules part substitutable (Non-Patent Literature 3), and that at the surface of a self-organized film of a benzyl phenyl sulfone compound having a silicon terminal, which is formed from benzyl-4-(2-(chlorodimethyl silyl)ethyl)phenyl sulfone (Non-Patent Literature 4) synthesized by reacting 4-benzylsulfonyl styrene with chlorodimethyl silane in the presence of platinum catalyst, the absorption band due to the surface benzene ring is reduced by UV-irrdatiation along with the decrease of the wettability (Non-Patent Literature 5).

In contrast, it is described in Patent Literature 1 that a part of a hexamethyldisilazane film adsorbed onto a resist is selectively exposed to electron beams to eliminate it, followed by performing oxygen plasma treatment to etch only the film-eliminated part of the resist. A patterning in which the fluorine content is lowered by photo irradiation to a composite layer containing a photocatalyst and fluorinated part is disclosed in Patent Literature 2. A method for patterning composed of a hydrophobic part and a hydrophilic part by which an intermediate layer having light degradable activity is provided between an uneven base layer and a hydrophobic monolayer, followed by selective elimination of the hydrophobic layer by light irradiation is disclosed in Patent Literature 3. Moreover, application to a resist or a memory medium utilizing partial conformational change of a porphyrin-copper complex in its monolayer induced by exposing the layer to radiation including ultraviolet irradiation or heat is disclosed in Patent Literature 4. It is disclosed in Patent Literature 5 that a part of an organic molecular film can be eliminated by exposing it to ultraviolet irradiation between 200 nm and 380 nm. Moreover, it is disclosed in Non-Patent Literature 6 and Patent Literature 6 that 2-nitrobenzyl ester, or ether compounds containing terminal silyl group are useful as surface modifying agents which can lower the contact angle by ultraviolet irradiation.

Although self-organized organic thin films and organic molecular adsorbed films are utilized for patterning in the aforementioned prior art, the molecular structure thereof is limited, the use of photo-irradiation with high energy wavelength is required, and the molecular structure required for controlling film properties which is important to achieve reliability has not been sufficiently studied, and so they are not necessarily sufficient to achieve high reliability or photosensitivity. For example, the compounds disclosed in Non-Patent Literature 4 have a limitation to their molecular structure, because of their production method, and lack the variety of partial molecular structure required to produce an excellent film as disclosed in Non-Patent Literature 7.

Non-Patent Literature 1: Science, 1991, Vol. 252, Pages 551 to 554
Non-Patent Literature 2: Langmuir, 1996, Vol. 12, Pages 1638 to 1650
Non-Patent Literature 3: Langmuir, 2000, Vol. 16, Pages 9963 to 9967
Non-Patent Literature 4: The Chemical Society of Japan, Proceedings of the 79th Spring Meeting, 2001, Page 591
Non-Patent Literature 5: The Chemical Society of Japan, Proceedings of the 81 st Spring Meeting, 2002, Page 192
Non-Patent Literature 6: Chem. Lett., 2000, Pages 228 to 229
Non-Patent Literature 7: J. Am. Chem. Soc., 1988, Vol. 110, Pages 6136 to 6144
Patent Literature 1: Japanese Patent Application, First Publication No. Hei 7-297100
Patent Literature 2: Japanese Patent Application, First Publication No. 2001-109103
Patent Literature 3: Japanese Patent Application, First Publication No. 2001-129474
Patent Literature 4: Japanese Patent Application, First Publication No. 2001-215719
Patent Literature 5: Japanese Patent Application, First Publication No. 2002-23356
Patent Literature 6: Japanese Patent Application, First Publication No. 2002-80481

DISCLOSURE OF INVENTION

The present invention has been achieved in view of the aforementioned prior art, and has as its object to provide a compound which is flexibly amenable to alteration of its molecular structural part which affects film forming ability and resulting surface properties, without impairing its photosensitivity, the compound being capable of undergoing surface alteration under irradiation with relatively low energy wavelength, and of forming an organic thin film on a substrate with good reproducibility, and an organic thin film formed body prepared by forming on its surface an organic thin film containing the compound.

As a result of diligent study to solve the aforementioned problems, the inventors of the present invention have found that compounds based on phenyl sulfone derivatives, into which connecting group through an oxygen atom and functional groups interacting with metal surfaces are introduced, can undergo surface alteration under irradiation with relatively low energy wavelength, and can form an organic thin film on a substrate with good reproducibility.

According to the first aspect of the present invention, a compound represented by formula (1)

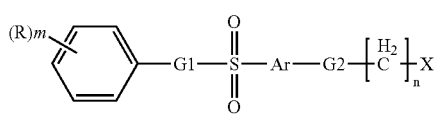
(1)

(wherein X represents a functional group containing a hetero atom and being able to interact with a surface of a metal or a metallic oxide, R represents a C1 to C20 alkyl group which may have a substituent, a C1 to C20 alkoxy group which may have a substitutent, an aryl group which may have a substituent, a C1 to C20 alkoxycarbonyl group which may have a substituent, or a halogen atom, and R may form a ring with another R; n represents an integer of 1 to 30, and m represents an integer of 0 to 5; R may be identical to, or may be different from each other, when m represents 2 or more; G1 represents a single bond or a C1 to C3 bivalent saturated or unsaturated hydrocarbon radical; Ar represents an aromatic group which may have a substituent; G2 represents O, S, or Nr; and r represents a hydrogen atom or a C1 to C4 alkyl group) is provided.

In the compound according to the present invention, it is preferable that X be a silyl group which may have a substituent in addition to chlorine atom or a C1 to C4 alkoxy group, mercapto group, a C1 to C4 alkylthio group which may have a substituent, a C1 to C10 acylthio group, a disulfide group, an amino group which may have a substituent, or a phosphono group which may have a substituent.

In the compound according to the present invention, it is preferable that Ar be a para-phenylene group which may have a substituent, a para-biphenylene group which may have a substituent, a para-triphenylene group which may have a substituent, or a naphthylene group which may have a substituent.

In the compound according to the present invention, it is preferable that R be a substituent which can exhibit liquid-repellence.

According to the second aspect of the present invention, an organic thin film formed body prepared by forming an organic thin film containing a compound represented by the formula (1) on the surface of a substrate is provided.

In the following, the compound represented by the aforementioned formula (1) according to the present invention and the organic thin film formed body will be explained in more detail.

The compound according to the present invention is represented by the aforementioned formula (1).

In the formula (1), X represents a functional group including a hetero atom and capable of interacting with a surface of a metal or a metallic oxide.

In the compound according to the present invention, it is preferable that X be a silyl group which may have a substituent in addition to a chlorine atom or a C1 to C4 alkoxy group, a mercapto group, a C1 to C4 alkylthio group which may have a substituent, a C1 to C10 acylthio group, a disulfide group, an amino group, or a phosphono group which may have a substituent.

Preferable examples of X include: silyl groups having chlorine atom, which may have a substituent such as a C1 to C4 alkyl group or an aryl group, such as chlorodihydrosilyl group, chlorodimethylsilyl group, chlorodiethylsilyl group, chlorodiphenylsilyl group, chloromethyl phenylsilyl group, dichlorohydrosilyl group, dichloromethylsilyl group, dichloroethylsilyl group, dichlorophenylsilyl group, trichlorosilyl group, or the like; silyl groups having a C1 to C4 alkoxy group, which may have a substituent such as a C1 to C4 alkyl group or an aryl group, such as trimethoxysilyl group, dimethoxymethylsilyl group, dimethoxychlorosilyl group, dimethoxyethylsilyl group, dimethoxyphenylsilyl group, triethoxysilyl group, diethoxymethylsilyl group, diethoxychlorosilyl group, diethoxyethylsilyl group, diethoxyphenylsilyl group, tripropoxysilyl group, dipropoxymethylsilyl group, dipropoxychlorosilyl group, dimethoxyethylsilyl group, or the like; mercapto group; C1 to C4 alkylthio groups which may have a substituent such as methylthio group, ethylthio group, methoxyethylthio group, carboxyethylthio group, or the like; C1 to C10 acylthio groups such as acetylthio group, propionylthio group, benzoylthio group, or the like; C1 to C4 alkyldisulfide groups such as methyldisulfide group, or the like, disulfide groups such as

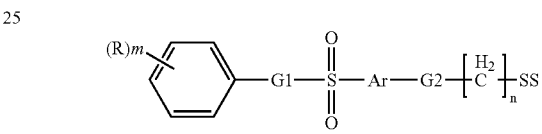

(wherein R, m, G1, Ar, G2, and n represent the same as described above), or the like; amino groups which may have a substituent such as C1 to C4 alkyl groups; phosphono groups which may have a substituent such as C1 to C4 alkyl groups or aryl groups, such as —P(=O)(OH)$_2$, —P(=O)(OCH$_3$)$_2$, —P(=O)(OC$_2$H$_5$)$_2$, —P(=O)(OC$_3$H$_7$)$_2$, —P(=O)(OC$_4$H$_9$)$_2$, —P(=O)(OPh)$_2$, or the like.

R represents a C1 to C20 alkyl group which may have a substituent, a C1 to C20 alkoxy group which may have a substituent, an aryl group which may have a substituent, a C1 to C20 alkoxycarbonyl group which may have a substituent, or a halogen atom, and two of R may form a ring, when m represents 2 or more. When two of R form a ring, a moiety of

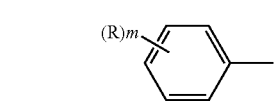

becomes a condensed ring such as naphthalene ring, anthracene ring, benzocyclobutene ring, or indan ring.

Examples of the C1 to C20 alkyl group include methyl group, ethyl group, propyl group, butyl group, t-butyl group, pentyl group, hexyl group, octyl group, nonyl group, decyl group, undecyl group, dodecyl group, and the like.

Although there are no particular limitations imposed on the substituent of the C1 to C20 alkyl group, examples thereof include: halogen atoms such as fluorine, chlorine, bromine, and the like; C1 to C4 alkoxy groups such as methoxy group, ethoxy group, and the like; cyano group; nitro group; C1 to C4 alkoxycarbonyl groups such as methoxycarbonyl group, ethoxycarbonyl group, and the like; C1 to C4 alkylthio groups such as methylthio group, ethylthio group, and the like; C1 to C4 alkylsulfonyl groups such as methylsulfonyl group, ethylsulfonyl group, and the like; and phenyl groups which may have a substituent such as a C1 to C4 alkyl group or a halogen atom, such as phenyl group, 4-methylphenyl group, pentafluorophenyl group, or the like.

Examples of the C1 to C20 alkoxy group include methoxy group, ethoxy group, propoxy group, isopropoxy group, butoxy group, t-butoxy group, pentyloxy group, hexyloxy group, octyloxy group, nonyloxy group, decyloxy group, and the like.

Although there are no particular limitations imposed on the substituent of the C1 to C20 alkoxy group, examples thereof include halogen atoms such as fluorine, chlorine, bromine, and the like; cyano group; nitro group; C1 to C4 alkoxycarbonyl groups such as methoxycarbonyl group, ethoxycarbonyl group, and the like; C1 to C4 alkylthio groups such as methylthio group, ethylthio group, and the like; C1 to C4 alkylsulfonyl groups such as methylsulfonyl group, ethylsulfonyl group, and the like; and phenyl groups which may have a substituent such as a C1 to C4 alkyl group or a halogen atom, such as phenyl group, 4-methylphenyl group, pentafluorophenyl group, or the like.

Examples of the aryl groups include phenyl group, 1-naphthyl group, 2-naphthyl group, 2-pyridyl group, 3-pyridyl group, 4-pyridyl group, 5-pyridyl group, and the like.

Although there are no particular limitations imposed on the substituent of the aryl group, examples thereof include halogen atoms such as fluorine, chlorine, bromine, and the like; C1 to C4 alkyl groups such as methyl group, ethyl group, and the like; C1 to C4 alkoxy groups such as methoxy group, ethoxy group, and the like; cyano group; nitro group; C1 to C4 alkoxycarbonyl groups such as methoxycarbonyl group, ethoxycarbonyl group, and the like, C1 to C4 alkylthio groups such as methylthio group, ethylthio group, and the like; C1 to C4 alkylsulfonyl groups such as methylsulfonyl group, ethylsulfonyl group, and the like; and phenyl groups which may have a substituent such as a C1 to C4 alkyl group or a halogen atom, such as phenyl group, 4-methylphenyl group, pentafluorophenyl group, or the like.

Examples of the C1 to C20 alkoxycarbonyl groups include methoxycarbonyl group, propoxycarbonyl group, and the like.

Although there are no particular limitations imposed on the substituent of the C1 to C20 acyloxycarbonyl group, examples thereof include halogen atoms such as fluorine, chlorine, bromine, and the like; C1 to C4 alkyl groups such as methyl group, ethyl group, and the like; C1 to C4 alkoxy groups such as methoxy group, ethoxy group, and the like; cyano group; nitro group; C1 to C4 alkoxycarbonyl groups such as methoxycarbonyl group, ethoxycarbonyl group, and the like, C1 to C4 alkylthio groups such as methylthio group, ethylthio group, and the like; C1 to C4 alkylsulfonyl groups such as methylsulfonyl group, ethylsulfonyl group, and the like; and phenyl groups which may have a substituent such as a C1 to C4 alkyl group or a halogen atom, such as phenyl group, 4-methylphenyl group, pentafluorophenyl group, or the like.

Examples of the halogen atoms include fluorine, chlorine, bromine, iodide, and the like.

These C1 to C20 alkyl groups, C1 to C20 alkoxy groups, aryl groups, and C1 to C20 alkoxycarbonyl groups may have substituents at their optional positions, and may have plural substituents which are the same as or different from each other.

Examples of the condensed ring group include naphthyl group, anthranyl group, indanyl, benzocyclobutane, and the like, and the condensed ring may have a substituent.

Although there are no particular limitations imposed on the substituent of the condensed ring, examples thereof include halogen atoms such as fluorine, chlorine, bromine, and the like; C1 to C4 alkyl groups such as methyl group, ethyl group, and the like; C1 to C4 alkoxy groups such as methoxy group, ethoxy group, and the like; cyano group; nitro group; C1 to C4 alkoxycarbonyl groups such as methoxycarbonyl group, ethoxycarbonyl group, and the like, C1 to C4 alkylthio groups such as methylthio group, ethylthio group, and the like; C1 to C4 alkylsulfonyl groups such as methylsulfonyl group, ethylsulfonyl group, and the like; and phenyl groups which may have a substituent such as a C1 to C4 alkyl group or a halogen atom, such as phenyl group, 4-methylphenyl group, pentafluorophenyl group, or the like.

Among these, it is preferable that R be a substituent which can exhibit liquid-repellence. The liquid-repellence means both of hydrophobicity and oleophobicity. Examples of the substituent having liquid-repellence include fluorine atom, C1 to C20 alkyl groups, C1 to C20 fluoroalkyl groups, C1 to C20 alkoxy groups, C1 to C20 fluoroalkoxy groups, aryl groups, and the like.

n represents an integer from 1 to 30.

m represents an integer from 0 to 5, and any particular R may be the same as or different from another R, when m represents 2 or more.

G1 represents a single bond or a C1 to C3 bivalent saturated or unsaturated hydrocarbon radical.

Ar represents an aromatic group which may have a substituent.

Examples of the aromatic group include phenylene groups, biphenylene groups, triphenylene groups, naphthylene groups, and the like. Among these, para-phenylene groups, para-biphenylene groups, para-triphenylene groups, or naphthylene groups are preferable.

G2 represents O, S, or Nr, and preferably represents O. r represents a hydrogen atom or a C1 to C4 alkyl group such as a methyl group.

(Production Method)

The compound represented by the formula (1) according to the present invention can be produced, for example, in accordance with the following. The general production method is shown hereinafter.

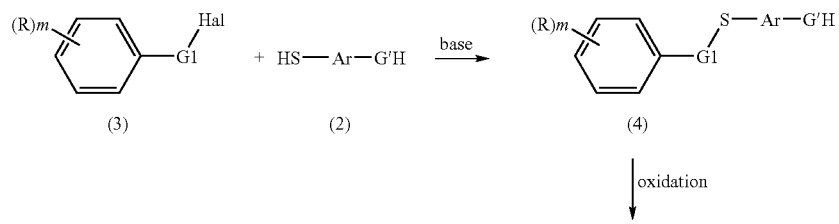

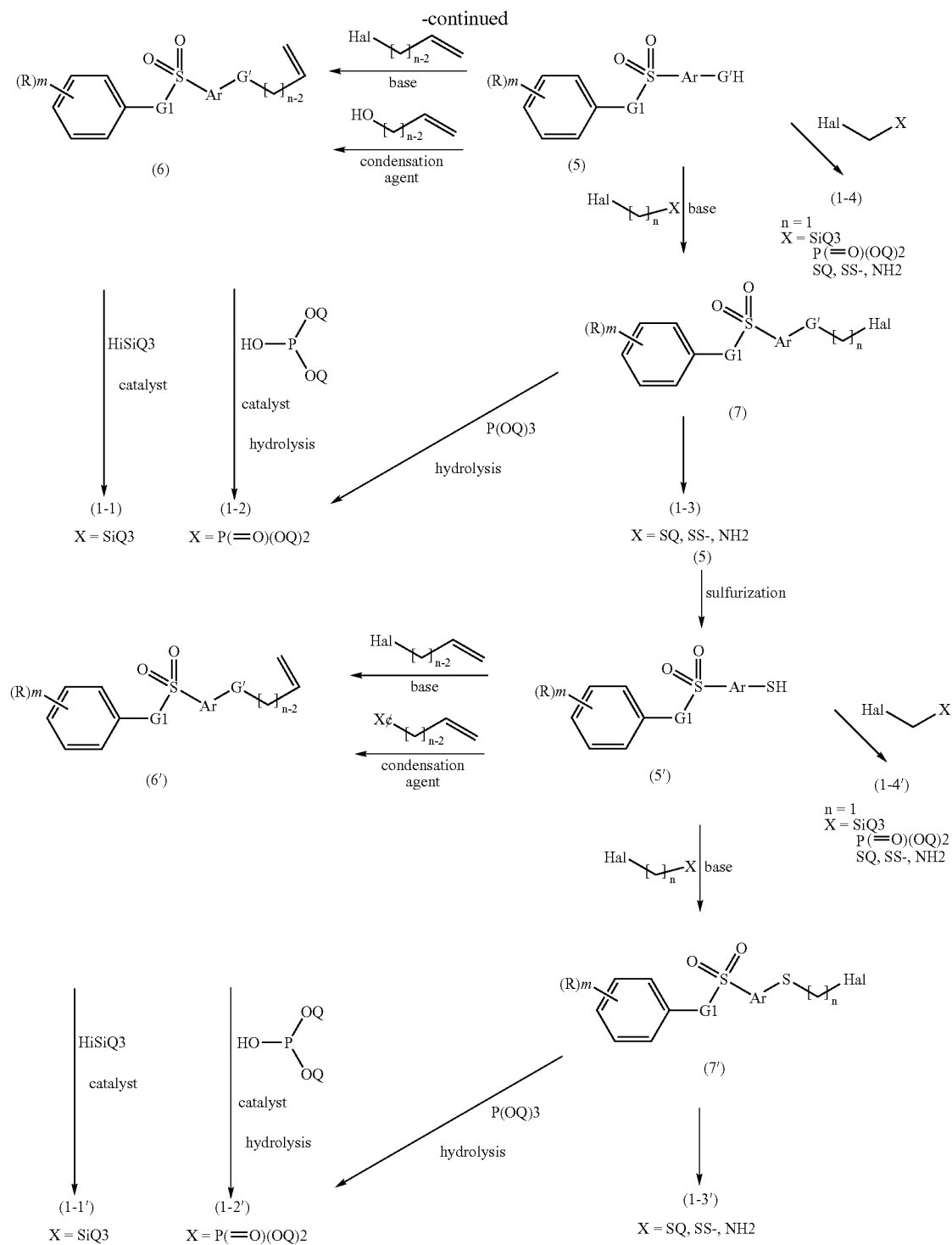

(In the formula, R, G1, Ar, n, m and X represent the same as described above. Hal represents a halogen atom, G' represents O, or Nr, and Q represents hydrogen atom, or a substituent such as a halogen atom such as chlorine atom; a C1 to C4 alkyl group such as methyl group, ethyl group, or the like; a C1 to C4 alkoxy group such as methoxy group, ethoxy group, or the like; or a phenyl group which may have a substituent, such as phenyl group.)

(Production Method 1) Production of a Compound in which X is a Silyl Group.

First of all, a sulfide compound (4) is produced by reacting a compound having a corresponding substituent R with an aromatic compound (2) in the presence of a base of 1 to 2 equivalents. Next, the produced sulfide compound (4) is oxidized by using a suitable oxidizing reagent to produce a corresponding sulfone (5). The sulfone (5) is then reacted with an alkylhalide or alcohol of which the terminal is olefin in the presence of a base or a condensation agent, to produce an olefin (6). The produced olefin (6) is then further reacted with a hydrosilane in the presence of a suitable catalyst to produce a compound (1-1) in which X is a silyl group.

Examples of the base usable in the aforementioned reaction include tertiary amines such as triethylamine, tributylamine, and the like; metallic alkoxides such as sodium methoxide, sodium ethoxide, potassium t-butoxide, and the like; and alkaline metal hydroxides such as sodium hydroxide, and the like; and alkaline metal carbonates such as potassium carbonate, and the like. Examples of usable oxidizing reagent include peroxides such as hydrogen peroxide, peracetic acid, m-chloroperbenzoic acid, and the like. Examples of the condensation agent used include compositions of azodicarboxylic acid esters such as azodicarboxylic acid diethyl ester and phosphines such as triphenylphosphine. Examples of the catalyst used in the reaction using hydrosilane include transition metals such as platinum, palladium, nickel, ruthenium, rhodium, and the like, and organic metal complexes thereof.

(Production Method 2) Production of a Compound in which X is a Phosphono Group.

A compound (1-2) in which X is a phosphono group can be produced by reacting a compound (6) with a phosphorous acid diester in the presence of a suitable catalyst, followed by hydrolysis. Examples of the catalyst used in the reaction with phosphorous acid diester include transition metals such as platinum, palladium, nickel, ruthenium, rhodium, and the like, halides thereof, and organic metal complexes thereof. The compound in which X is a phosphono group can also be produced by reacting a compound (7) described below with a phosphorous acid triester, followed by hydrolysis.

(Production Method 3) Production of a Compound in which X is a Mercapto Group, a C1 to C4 Alkylthio Group, or an Amino Group.

A compound (1-3) in which X is a mercapto group, a C1 to C4 alkylthio group, or an amino group can be produced by reacting the compound (5) with α, ω-dihaloalkane to produce the compound (7), followed by nucleophilic substitution reaction with a sulfur or nitrogen atom.

(Production Method 4) Production of a Compound in which X is a Disulfide Group.

A compound (1-3) in which X is a disulfide group can be produced by oxidatively dimerizing a compound in which X is mercapto group.

(Production Method 5) Production of a Compound in which k is 0.

This can be produced in accordance with the aforementioned production methods 1 to 4 for introducing X by using a compound produced by alkylating only one hydroxyl group of 4,4'-dihydroxydiphenyl sulfone used as a starting material, and by reacting the other hydroxyl group with an alkylating agent of which the terminal is an olefin or a halogen atom.

There are no particular limitations imposed on the solvents which can be used in the aforementioned production methods 1 to 5, provided that they are solvents inert during the reaction. Examples thereof include water; alcohols such as methanol, ethanol, and the like; nitrites such as acetonitrile; ethers such as diethylether, 1,2-dimethoxyethane, tetrahydrofuran (THF), and the like; aromatic hydrocarbons such as benzene, toluene, xylene, and the like; halogenated hydrocarbons such as dichloromethane, chloroform, and the like; and mixtures of two or more of these. Moreover, a two phase system of water-organic solvents may be used. The reaction is smoothly carried out between −80° C. and +200° C.

After the end of all of the reactions, objective materials can be separated and purified by conventional organic synthetic method. The structure of the objective materials can be confirmed by measurement of NMR spectrum, mass spectrum, or IR spectrum, elemental analysis, or the like.

Examples of the compound (compound represented by the formula (1)) according to the present invention, which is produced as described above, are shown in Table 1. In Table 1, A1 to A4 represent the following groups.

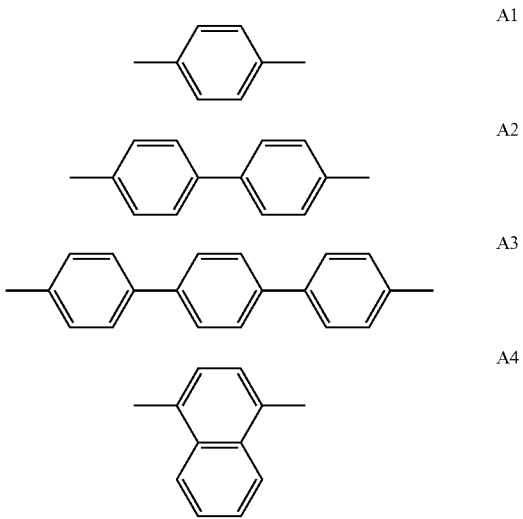

TABLE 1

| Compound No. | (R)m | k | Ar | G2 | n | X | Physical Properties [Melting Point] |
|---|---|---|---|---|---|---|---|
| 1 | 4-CH3 | 1 | A1 | O | 3 | Si(OMe)3 | |
| 2 | 4-CH3 | 1 | A1 | O | 4 | Si(OMe)3 | NMR* |
| 3 | 4-CH3 | 1 | A1 | O | 4 | Si(OEt)3 | NMR* |
| 4 | 4-CH3 | 1 | A1 | O | 4 | SiCl3 | |
| 5 | 4-CH3 | 1 | A1 | O | 4 | PO(OH)2 | |
| 6 | 4-CH3 | 1 | A1 | O | 10 | Si(OMe)3 | [68-76° C.] |
| 7 | 4-CH3 | 1 | A1 | O | 10 | Si(OEt)3 | [73-74° C.] |
| 8 | 4-CH3 | 1 | A1 | O | 10 | SiCl3 | |

TABLE 1-continued

| | | | | | | | |
|---|---|---|---|---|---|---|---|
| 9  | 4-CH3  | 1 | A1 | O | 10 | SiMe2Cl  | [98-99° C.] |
| 10 | 4-CH3  | 1 | A1 | O | 10 | PO(OH)2  | |
| 11 | 4-CH3  | 1 | A1 | O | 12 | PO(OH)2  | [148-150° C.] |
| 12 | 4-CH3  | 1 | A1 | O | 12 | PO(OEt)2 | NMR* |
| 13 | 4-CH3  | 1 | A2 | O | 4  | Si(OMe)3 | |
| 14 | 4-CH3  | 1 | A2 | O | 4  | Si(OEt)3 | |
| 15 | 4-CH3  | 1 | A2 | O | 4  | SiCl3    | |
| 16 | 4-CH3  | 1 | A2 | O | 4  | PO(OH)2  | |
| 17 | 4-CH3  | 1 | A2 | O | 10 | Si(OMe)3 | |
| 18 | 4-CH3  | 1 | A2 | O | 10 | Si(OEt)3 | |
| 19 | 4-CH3  | 1 | A2 | O | 10 | SiCl3    | |
| 20 | 4-CH3  | 1 | A2 | O | 10 | PO(OH)2  | |
| 21 | 4-CH3  | 1 | A2 | O | 12 | PO(OH)2  | |
| 22 | 4-CH3  | 1 | A3 | O | 3  | Si(OMe)3 | |
| 23 | 4-CH3  | 1 | A3 | O | 4  | Si(OEt)3 | |
| 24 | 4-CH3  | 1 | A3 | O | 4  | SiCl3    | |
| 25 | 4-CH3  | 1 | A3 | O | 4  | PO(OH)2  | |
| 26 | 4-CH3  | 1 | A3 | O | 10 | Si(OMe)3 | |
| 27 | 4-CH3  | 1 | A3 | O | 10 | Si(OEt)3 | |
| 28 | 4-CH3  | 1 | A3 | O | 10 | SiCl3    | |
| 29 | 4-CH3  | 1 | A3 | O | 10 | PO(OH)2  | |
| 30 | 4-CH3  | 1 | A3 | O | 12 | PO(OH)2  | |
| 31 | 4-CH3  | 1 | A4 | O | 3  | Si(OMe)3 | |
| 32 | 4-CH3  | 1 | A4 | O | 4  | Si(OMe)3 | |
| 33 | 4-CH3  | 1 | A4 | O | 4  | Si(OEt)3 | |
| 34 | 4-CH3  | 1 | A4 | O | 4  | SiCl3    | |
| 35 | 4-CH3  | 1 | A4 | O | 4  | PO(OH)2  | |
| 36 | 4-CH3  | 1 | A4 | O | 10 | Si(OMe)3 | |
| 37 | 4-CH3  | 1 | A4 | O | 10 | Si(OEt)3 | |
| 38 | 4-CH3  | 1 | A4 | O | 10 | SiCl3    | |
| 39 | 4-CH3  | 1 | A4 | O | 10 | PO(OH)2  | |
| 40 | 4-CH3  | 1 | A4 | O | 12 | PO(OH)2  | |
| 41 | 4-CF3  | 1 | A1 | O | 3  | Si(OMe)3 | |
| 42 | 4-CF3  | 1 | A1 | O | 4  | Si(OMe)3 | |
| 43 | 4-CF3  | 1 | A1 | O | 4  | Si(OEt)3 | [124-128° C.] |
| 44 | 4-CF3  | 1 | A1 | O | 4  | SiCl3    | |
| 45 | 4-CF3  | 1 | A1 | O | 4  | PO(OH)2  | |
| 46 | 4-CF3  | 1 | A1 | O | 5  | Si(OMe)3 | |
| 47 | 4-CF3  | 1 | A1 | O | 5  | Si(OEt)3 | [138-140° C.] |
| 48 | 4-CF3  | 1 | A1 | O | 5  | SiCl3    | |
| 49 | 4-CF3  | 1 | A1 | O | 10 | Si(OMe)3 | [146.5-149° C.] |
| 50 | 4-CF3  | 1 | A1 | O | 10 | Si(OEt)3 | [147-149° C.] |
| 51 | 4-CF3  | 1 | A1 | O | 10 | SiCl3    | |
| 52 | 4-CF3  | 1 | A1 | O | 10 | SiMe2Cl  | |
| 53 | 4-CF3  | 1 | A1 | O | 10 | PO(OH)2  | |
| 54 | 4-CF3  | 1 | A1 | O | 12 | PO(OH)2  | |
| 55 | 4-CF3  | 1 | A1 | O | 12 | PO(OMe)2 | NMR* |
| 56 | 4-CF3  | 1 | A1 | O | 23 | Si(OEt)3 | [137-146° C.] |
| 57 | 4-CF3  | 1 | A2 | O | 3  | Si(OMe)3 | |
| 58 | 4-CF3  | 1 | A2 | O | 4  | Si(OMe)3 | |
| 59 | 4-CF3  | 1 | A2 | O | 4  | Si(OEt)3 | |
| 60 | 4-CF3  | 1 | A2 | O | 4  | SiCl3    | |
| 61 | 4-CF3  | 1 | A2 | O | 4  | PO(OH)2  | |
| 62 | 4-CF3  | 1 | A2 | O | 10 | Si(OMe)3 | |
| 63 | 4-CF3  | 1 | A2 | O | 10 | Si(OEt)3 | |
| 64 | 4-CF3  | 1 | A2 | O | 10 | SiCl3    | |
| 65 | 4-CF3  | 1 | A2 | O | 10 | PO(OH)2  | |
| 66 | 4-CF3  | 1 | A2 | O | 12 | PO(OH)2  | |
| 67 | 4-CF3  | 1 | A3 | O | 3  | Si(OMe)3 | |
| 68 | 4-CF3  | 1 | A3 | O | 4  | Si(OMe)3 | |
| 69 | 4-CF3  | 1 | A3 | O | 4  | Si(OEt)3 | |
| 70 | 4-CF3  | 1 | A3 | O | 4  | SiCl3    | |
| 71 | 4-CF3  | 1 | A3 | O | 4  | PO(OH)2  | |
| 72 | 4-CF3  | 1 | A3 | O | 10 | Si(OMe)3 | |
| 73 | 4-CF3  | 1 | A3 | O | 10 | Si(OEt)3 | |
| 74 | 4-CF3  | 1 | A3 | O | 10 | SiCl3    | |
| 75 | 4-CF3  | 1 | A3 | O | 10 | PO(OH)2  | |
| 76 | 4-CF3  | 1 | A3 | O | 12 | PO(OH)2  | |
| 77 | 4-CF3  | 1 | A4 | O | 3  | Si(OMe)3 | |
| 78 | 4-CF3  | 1 | A4 | O | 4  | Si(OMe)3 | |
| 79 | 4-CF3  | 1 | A4 | O | 4  | Si(OEt)3 | |
| 80 | 4-CF3  | 1 | A4 | O | 4  | SiCl3    | |
| 81 | 4-CF3  | 1 | A4 | O | 4  | PO(OH)2  | |
| 82 | 4-CF3  | 1 | A4 | O | 10 | Si(OMe)3 | |
| 83 | 4-CF3  | 1 | A4 | O | 10 | Si(OEt)3 | |
| 84 | 4-CF3  | 1 | A4 | O | 10 | SiCl3    | |
| 85 | 4-CF3  | 1 | A4 | O | 10 | PO(OH)2  | |
| 86 | 4-CF3  | 1 | A4 | O | 12 | PO(OH)2  | |
| 87 | 4-CF3O | 1 | A1 | O | 3  | Si(OMe)3 | |

TABLE 1-continued

| | | | | | | |
|---|---|---|---|---|---|---|
| 88 | 4-CF3O | 1 | A1 | O | 4 | Si(OMe)3 |
| 89 | 4-CF3O | 1 | A1 | O | 4 | Si(OEt)3 |
| 90 | 4-CF3O | 1 | A1 | O | 4 | SiCl3 |
| 91 | 4-CF3O | 1 | A1 | O | 4 | PO(OH)2 |
| 92 | 4-CF3O | 1 | A1 | O | 10 | Si(OMe)3 |
| 93 | 4-CF3O | 1 | A1 | O | 10 | Si(OEt)3 |
| 94 | 4-CF3O | 1 | A1 | O | 10 | SiCl3 |
| 95 | 4-CF3O | 1 | A1 | O | 10 | PO(OH)2 |
| 96 | 4-CF3O | 1 | A1 | O | 12 | PO(OH)2 |
| 97 | 4-CF3O | 1 | A2 | O | 3 | Si(OMe)3 |
| 98 | 4-CF3O | 1 | A2 | O | 4 | Si(OMe)3 |
| 99 | 4-CF3O | 1 | A2 | O | 4 | Si(OEt)3 |
| 100 | 4-CF3O | 1 | A2 | O | 4 | SiCl3 |
| 101 | 4-CF3O | 1 | A2 | O | 4 | PO(OH)2 |
| 102 | 4-CF3O | 1 | A2 | O | 10 | Si(OMe)3 |
| 103 | 4-CF3O | 1 | A2 | O | 10 | Si(OEt)3 |
| 104 | 4-CF3O | 1 | A2 | O | 10 | SiCl3 |
| 105 | 4-CF3O | 1 | A2 | O | 10 | PO(OH)2 |
| 106 | 4-CF3O | 1 | A2 | O | 12 | PO(OH)2 |
| 107 | 4-CF3O | 1 | A3 | O | 3 | Si(OMe)3 |
| 108 | 4-CF3O | 1 | A3 | O | 4 | Si(OMe)3 |
| 109 | 4-CF3O | 1 | A3 | O | 4 | Si(OEt)3 |
| 110 | 4-CF3O | 1 | A3 | O | 4 | SiCl3 |
| 111 | 4-CF3O | 1 | A3 | O | 4 | PO(OH)2 |
| 112 | 4-CF3O | 1 | A3 | O | 10 | Si(OMe)3 |
| 113 | 4-CF3O | 1 | A3 | O | 10 | Si(OEt)3 |
| 114 | 4-CF3O | 1 | A3 | O | 10 | SiCl3 |
| 115 | 4-CF3O | 1 | A3 | O | 10 | PO(OH)2 |
| 116 | 4-CF3O | 1 | A3 | O | 12 | PO(OH)2 |
| 117 | 4-CF3O | 1 | A4 | O | 3 | Si(OMe)3 |
| 118 | 4-CF3O | 1 | A4 | O | 4 | Si(OMe)3 |
| 119 | 4-CF3O | 1 | A4 | O | 4 | Si(OEt)3 |
| 120 | 4-CF3O | 1 | A4 | O | 4 | SiCl3 |
| 121 | 4-CF3O | 1 | A4 | O | 4 | PO(OH)2 |
| 122 | 4-CF3O | 1 | A4 | O | 10 | Si(OMe)3 |
| 123 | 4-CF3O | 1 | A4 | O | 10 | Si(OEt)3 |
| 124 | 4-CF3O | 1 | A4 | O | 10 | SiCl3 |
| 125 | 4-CF3O | 1 | A4 | O | 10 | PO(OH)2 |
| 126 | 4-CF3O | 1 | A4 | O | 12 | PO(OH)2 |
| 127 | 4-t-Bu | 1 | A1 | O | 3 | Si(OMe)3 |
| 128 | 4-t-Bu | 1 | A1 | O | 4 | Si(OMe)3 |
| 129 | 4-t-Bu | 1 | A1 | O | 4 | Si(OEt)3 |
| 130 | 4-t-Bu | 1 | A1 | O | 4 | SiCl3 |
| 131 | 4-t-Bu | 1 | A1 | O | 4 | PO(OH)2 |
| 132 | 4-t-Bu | 1 | A1 | O | 10 | Si(OMe)3 |
| 133 | 4-t-Bu | 1 | A1 | O | 10 | Si(OEt)3 |
| 134 | 4-t-Bu | 1 | A1 | O | 10 | SiCl3 |
| 135 | 4-t-Bu | 1 | A1 | O | 10 | PO(OH)2 |
| 136 | 4-t-Bu | 1 | A1 | O | 12 | PO(OH)2 |
| 137 | 4-t-Bu | 1 | A2 | O | 3 | Si(OMe)3 |
| 138 | 4-t-Bu | 1 | A2 | O | 4 | Si(OMe)3 |
| 139 | 4-t-Bu | 1 | A2 | O | 4 | Si(OEt)3 |
| 140 | 4-t-Bu | 1 | A2 | O | 4 | SiCl3 |
| 141 | 4-t-Bu | 1 | A2 | O | 4 | PO(OH)2 |
| 142 | 4-t-Bu | 1 | A2 | O | 10 | Si(OMe)3 |
| 143 | 4-t-Bu | 1 | A2 | O | 10 | Si(OEt)3 |
| 144 | 4-t-Bu | 1 | A2 | O | 10 | SiCl3 |
| 145 | 4-t-Bu | 1 | A2 | O | 10 | PO(OH)2 |
| 146 | 4-t-Bu | 1 | A2 | O | 12 | PO(OH)2 |
| 147 | 4-t-Bu | 1 | A3 | O | 3 | Si(OMe)3 |
| 148 | 4-t-Bu | 1 | A3 | O | 4 | Si(OMe)3 |
| 149 | 4-t-Bu | 1 | A3 | O | 4 | Si(OEt)3 |
| 150 | 4-t-Bu | 1 | A3 | O | 4 | SiCl3 |
| 151 | 4-t-Bu | 1 | A3 | O | 4 | PO(OH)2 |
| 152 | 4-t-Bu | 1 | A3 | O | 10 | Si(OMe)3 |
| 153 | 4-t-Bu | 1 | A3 | O | 10 | Si(OEt)3 |
| 154 | 4-t-Bu | 1 | A3 | O | 10 | SiCl3 |
| 155 | 4-t-Bu | 1 | A3 | O | 10 | PO(OH)2 |
| 156 | 4-t-Bu | 1 | A3 | O | 12 | PO(OH)2 |
| 157 | 4-t-Bu | 1 | A4 | O | 3 | Si(OMe)3 |
| 158 | 4-t-Bu | 1 | A4 | O | 4 | Si(OMe)3 |
| 159 | 4-t-Bu | 1 | A4 | O | 4 | Si(OEt)3 |
| 160 | 4-t-Bu | 1 | A4 | O | 4 | SiCl3 |
| 161 | 4-t-Bu | 1 | A4 | O | 4 | PO(OH)2 |
| 162 | 4-t-Bu | 1 | A4 | O | 10 | Si(OMe)3 |
| 163 | 4-t-Bu | 1 | A4 | O | 10 | Si(OEt)3 |
| 164 | 4-t-Bu | 1 | A4 | O | 10 | SiCl3 |
| 165 | 4-t-Bu | 1 | A4 | O | 10 | PO(OH)2 |
| 166 | 4-t-Bu | 1 | A4 | O | 12 | PO(OH)2 |

TABLE 1-continued

| | | | | | | | |
|---|---|---|---|---|---|---|---|
| 167 | 4-n-C10H21 | 1 | A1 | O | 3 | Si(OMe)3 | |
| 168 | 4-n-C10H21 | 1 | A1 | O | 4 | Si(OMe)3 | |
| 169 | 4-n-C10H21 | 1 | A1 | O | 4 | Si(OEt)3 | NMR* |
| 170 | 4-n-C10H21 | 1 | A1 | O | 4 | SiCl3 | |
| 171 | 4-n-C10H21 | 1 | A1 | O | 4 | PO(OH)2 | |
| 172 | 4-n-C10H21 | 1 | A1 | O | 10 | Si(OMe)3 | |
| 173 | 4-n-C10H21 | 1 | A1 | O | 10 | Si(OEt)3 | |
| 174 | 4-n-C10H21 | 1 | A1 | O | 10 | SiMe2Cl | |
| 175 | 4-n-C10H21 | 1 | A1 | O | 10 | SiCl3 | |
| 176 | 4-n-C10H21 | 1 | A1 | O | 10 | PO(OH)2 | |
| 177 | 4-n-C10H21 | 1 | A1 | O | 12 | PO(OH)2 | |
| 178 | 4-n-C10H21 | 1 | A2 | O | 3 | Si(OMe)3 | |
| 179 | 4-n-C10H21 | 1 | A2 | O | 4 | Si(OMe)3 | |
| 180 | 4-n-C10H21 | 1 | A2 | O | 4 | Si(OEt)3 | |
| 181 | 4-n-C10H21 | 1 | A2 | O | 4 | SiCl3 | |
| 182 | 4-n-C10H21 | 1 | A2 | O | 4 | PO(OH)2 | |
| 183 | 4-n-C10H21 | 1 | A2 | O | 10 | Si(OMe)3 | |
| 184 | 4-n-C10H21 | 1 | A2 | O | 10 | Si(OEt)3 | |
| 185 | 4-n-C10H21 | 1 | A2 | O | 10 | SiCl3 | |
| 186 | 4-n-C10H21 | 1 | A2 | O | 10 | PO(OH)2 | |
| 187 | 4-n-C10H21 | 1 | A2 | O | 12 | PO(OH)2 | |
| 188 | 4-n-C10H21 | 1 | A3 | O | 3 | Si(OMe)3 | |
| 189 | 4-n-C10H21 | 1 | A3 | O | 4 | Si(OMe)3 | |
| 190 | 4-n-C10H21 | 1 | A3 | O | 4 | Si(OEt)3 | |
| 191 | 4-n-C10H21 | 1 | A3 | O | 4 | SiCl3 | |
| 192 | 4-n-C10H21 | 1 | A3 | O | 4 | PO(OH)2 | |
| 193 | 4-n-C10H21 | 1 | A3 | O | 10 | Si(OMe)3 | |
| 194 | 4-n-C10H21 | 1 | A3 | O | 10 | Si(OEt)3 | |
| 195 | 4-n-C10H21 | 1 | A3 | O | 10 | SiCl3 | |
| 196 | 4-n-C10H21 | 1 | A3 | O | 10 | PO(OH)2 | |
| 197 | 4-n-C10H21 | 1 | A3 | O | 12 | PO(OH)2 | |
| 198 | 4-n-C10H21 | 1 | A4 | O | 3 | Si(OMe)3 | |
| 199 | 4-n-C10H21 | 1 | A4 | O | 4 | Si(OMe)3 | |
| 200 | 4-n-C10H21 | 1 | A4 | O | 4 | Si(OEt)3 | |
| 201 | 4-n-C10H21 | 1 | A4 | O | 4 | SiCl3 | |
| 202 | 4-n-C10H21 | 1 | A4 | O | 4 | PO(OH)2 | |
| 203 | 4-n-C10H21 | 1 | A4 | O | 10 | Si(OMe)3 | |
| 204 | 4-n-C10H21 | 1 | A4 | O | 10 | Si(OEt)3 | |
| 205 | 4-n-C10H21 | 1 | A4 | O | 10 | SiCl3 | |
| 206 | 4-n-C10H21 | 1 | A4 | O | 10 | PO(OH)2 | |
| 207 | 4-n-C10H21 | 1 | A4 | O | 12 | PO(OH)2 | |
| 208 | 4-n-C12H25 | 1 | A1 | O | 3 | Si(OMe)3 | |
| 209 | 4-n-C12H25 | 1 | A1 | O | 4 | Si(OMe)3 | |
| 210 | 4-n-C12H25 | 1 | A1 | O | 4 | Si(OEt)3 | |
| 211 | 4-n-C12H25 | 1 | A1 | O | 4 | SiCl3 | |
| 212 | 4-n-C12H25 | 1 | A1 | O | 5 | Si(OMe)3 | NMR* |
| 213 | 4-n-C12H25 | 1 | A1 | O | 10 | Si(OMe)3 | NMR* |
| 214 | 4-n-C12H25 | 1 | A1 | O | 10 | Si(OEt)3 | NMR* |
| 215 | 4-n-C12H25 | 1 | A1 | O | 10 | SiMe2Cl | |
| 216 | 4-n-C12H25 | 1 | A1 | O | 10 | SiCl3 | |
| 217 | 4-n-C12H25 | 1 | A1 | O | 10 | PO(OH)2 | |
| 218 | 4-n-C12H25 | 1 | A1 | O | 12 | PO(OH)2 | |
| 219 | 4-n-C12H25 | 1 | A2 | O | 3 | Si(OMe)3 | |
| 220 | 4-n-C12H25 | 1 | A2 | O | 4 | Si(OMe)3 | |
| 221 | 4-n-C12H25 | 1 | A2 | O | 4 | Si(OEt)3 | |
| 222 | 4-n-C12H25 | 1 | A2 | O | 4 | SiCl3 | |
| 223 | 4-n-C12H25 | 1 | A2 | O | 4 | PO(OH)2 | |
| 224 | 4-n-C12H25 | 1 | A2 | O | 10 | Si(OMe)3 | |
| 225 | 4-n-C12H25 | 1 | A2 | O | 10 | Si(OEt)3 | |
| 226 | 4-n-C12H25 | 1 | A2 | O | 10 | SiCl3 | |
| 227 | 4-n-C12H25 | 1 | A2 | O | 10 | PO(OH)2 | |
| 228 | 4-n-C12H25 | 1 | A2 | O | 12 | PO(OH)2 | |
| 229 | 4-n-C12H25 | 1 | A3 | O | 3 | Si(OMe)3 | |
| 230 | 4-n-C12H25 | 1 | A3 | O | 4 | Si(OMe)3 | |
| 231 | 4-n-C12H25 | 1 | A3 | O | 4 | Si(OEt)3 | |
| 232 | 4-n-C12H25 | 1 | A3 | O | 4 | SiCl3 | |
| 233 | 4-n-C12H25 | 1 | A3 | O | 4 | PO(OH)2 | |
| 234 | 4-n-C12H25 | 1 | A3 | O | 10 | Si(OMe)3 | |
| 235 | 4-n-C12H25 | 1 | A3 | O | 10 | Si(OEt)3 | |
| 236 | 4-n-C12H25 | 1 | A3 | O | 10 | SiCl3 | |
| 237 | 4-n-C12H25 | 1 | A3 | O | 10 | PO(OH)2 | |
| 238 | 4-n-C12H25 | 1 | A3 | O | 12 | PO(OH)2 | |
| 239 | 4-n-C12H25 | 1 | A4 | O | 3 | Si(OMe)3 | |
| 240 | 4-n-C12H25 | 1 | A4 | O | 4 | Si(OMe)3 | |
| 241 | 4-n-C12H25 | 1 | A4 | O | 4 | Si(OEt)3 | |
| 242 | 4-n-C12H25 | 1 | A4 | O | 4 | SiCl3 | |
| 243 | 4-n-C12H25 | 1 | A4 | O | 4 | PO(OH)2 | |
| 244 | 4-n-C12H25 | 1 | A4 | O | 10 | Si(OMe)3 | |
| 245 | 4-n-C12H25 | 1 | A4 | O | 10 | Si(OEt)3 | |

TABLE 1-continued

| | | | | | | | |
|---|---|---|---|---|---|---|---|
| 246 | 4-n-C12H25 | 1 | A4 | O | 10 | SiCl3 | |
| 247 | 4-n-C12H25 | 1 | A4 | O | 10 | PO(OH)2 | |
| 248 | 4-n-C12H25 | 1 | A4 | O | 12 | PO(OH)2 | |
| 249 | pentafluoro | 1 | A1 | O | 3 | Si(OMe)3 | |
| 250 | pentafluoro | 1 | A1 | O | 4 | Si(OMe)3 | |
| 251 | pentafluoro | 1 | A1 | O | 4 | Si(OEt)3 | NMR* |
| 252 | pentafluoro | 1 | A1 | O | 4 | SiCl3 | |
| 253 | pentafluoro | 1 | A1 | O | 4 | PO(OH)2 | |
| 254 | pentafluoro | 1 | A1 | O | 5 | Si(OEt)3 | [69-73° C.] |
| 255 | pentafluoro | 1 | A1 | O | 10 | Si(OMe)3 | |
| 256 | pentafluoro | 1 | A1 | O | 10 | Si(OEt)3 | [114-118° C.] |
| 257 | pentafluoro | 1 | A1 | O | 10 | SiCl3 | |
| 258 | pentafluoro | 1 | A1 | O | 10 | PO(OH)2 | |
| 259 | pentafluoro | 1 | A1 | O | 12 | PO(OH)2 | |
| 260 | pentafluoro | 1 | A4 | O | 3 | Si(OMe)3 | |
| 261 | pentafluoro | 1 | A4 | O | 4 | Si(OMe)3 | |
| 262 | pentafluoro | 1 | A4 | O | 4 | SiCl3 | |
| 263 | pentafluoro | 1 | A4 | O | 4 | SiCl3 | |
| 264 | pentafluoro | 1 | A4 | O | 4 | PO(OH)2 | |
| 265 | pentafluoro | 1 | A4 | O | 10 | Si(OMe)3 | |
| 266 | pentafluoro | 1 | A4 | O | 10 | Si(OEt)3 | |
| 267 | pentafluoro | 1 | A4 | O | 10 | SiCl3 | |
| 268 | pentafluoro | 1 | A4 | O | 10 | PO(OH)2 | |
| 269 | pentafluoro | 1 | A4 | O | 12 | PO(OH)2 | |
| 270 | pentafluoro | 1 | A2 | O | 3 | Si(OMe)3 | |
| 271 | pentafluoro | 1 | A2 | O | 4 | Si(OMe)3 | |
| 272 | pentafluoro | 1 | A2 | O | 4 | Si(OEt)3 | |
| 273 | pentafluoro | 1 | A2 | O | 4 | SiCl3 | |
| 274 | pentafluoro | 1 | A2 | O | 4 | PO(OH)2 | |
| 275 | pentafluoro | 1 | A2 | O | 10 | Si(OMe)3 | |
| 276 | pentafluoro | 1 | A2 | O | 10 | Si(OEt)3 | |
| 277 | pentafluoro | 1 | A2 | O | 10 | SiCl3 | |
| 278 | pentafluoro | 1 | A2 | O | 10 | PO(OH)2 | |
| 279 | pentafluoro | 1 | A2 | O | 12 | PO(OH)2 | |
| 280 | pentafluoro | 1 | A3 | O | 3 | Si(OMe)3 | |
| 281 | pentafluoro | 1 | A3 | O | 4 | Si(OMe)3 | |
| 282 | pentafluoro | 1 | A3 | O | 4 | Si(OEt)3 | |
| 283 | pentafluoro | 1 | A3 | O | 4 | SiCl3 | |
| 284 | pentafluoro | 1 | A3 | O | 4 | PO(OH)2 | |
| 285 | pentafluoro | 1 | A3 | O | 10 | Si(OMe)3 | |
| 286 | pentafluoro | 1 | A3 | O | 10 | Si(OEt)3 | |
| 287 | pentafluoro | 1 | A3 | O | 10 | SiCl3 | |
| 288 | pentafluoro | 1 | A3 | O | 10 | PO(OH)2 | |
| 289 | pentafluoro | 1 | A3 | O | 12 | PO(OH)2 | |
| 290 | 4-n-C10H21O | 1 | A1 | O | 3 | Si(OMe)3 | |
| 291 | 4-n-C10H21O | 1 | A1 | O | 4 | Si(OMe)3 | |
| 292 | 4-n-C10H21O | 1 | A1 | O | 4 | Si(OEt)3 | |
| 293 | 4-n-C10H21O | 1 | A1 | O | 4 | SiCl3 | |
| 294 | 4-n-C10H21O | 1 | A1 | O | 4 | PO(OH)2 | |
| 295 | 4-n-C10H21O | 1 | A1 | O | 10 | Si(OMe)3 | |
| 296 | 4-n-C10H21O | 1 | A1 | O | 10 | Si(OEt)3 | |
| 297 | 4-n-C10H21O | 1 | A1 | O | 10 | SiCl3 | |
| 298 | 4-n-C10H21O | 1 | A1 | O | 10 | PO(OH)2 | |
| 299 | 4-n-C10H21O | 1 | A1 | O | 12 | PO(OH)2 | |
| 300 | 4-n-C10H21O | 1 | A2 | O | 3 | Si(OMe)3 | |
| 301 | 4-n-C10H21O | 1 | A2 | O | 4 | Si(OMe)3 | |
| 302 | 4-n-C10H21O | 1 | A2 | O | 4 | Si(OEt)3 | |
| 303 | 4-n-C10H21O | 1 | A2 | O | 4 | SiCl3 | |
| 304 | 4-n-C10H21O | 1 | A2 | O | 4 | PO(OH)2 | |
| 305 | 4-n-C10H21O | 1 | A2 | O | 10 | Si(OMe)3 | |
| 306 | 4-n-C10H21O | 1 | A2 | O | 10 | Si(OEt)3 | |
| 307 | 4-n-C10H21O | 1 | A2 | O | 10 | SiCl3 | |
| 308 | 4-n-C10H21O | 1 | A2 | O | 10 | PO(OH)2 | |
| 309 | 4-n-C10H21O | 1 | A2 | O | 12 | PO(OH)2 | |
| 310 | 4-n-C10H21O | 1 | A3 | O | 3 | Si(OMe)3 | |
| 311 | 4-n-C10H21O | 1 | A3 | O | 4 | Si(OMe)3 | |
| 312 | 4-n-C10H21O | 1 | A3 | O | 4 | Si(OEt)3 | |
| 313 | 4-n-C10H21O | 1 | A3 | O | 4 | SiCl3 | |
| 314 | 4-n-C10H21O | 1 | A3 | O | 4 | PO(OH)2 | |
| 315 | 4-n-C10H21O | 1 | A3 | O | 10 | Si(OMe)3 | |
| 316 | 4-n-C10H21O | 1 | A3 | O | 10 | Si(OEt)3 | |
| 317 | 4-n-C10H21O | 1 | A3 | O | 10 | SiCl3 | |
| 318 | 4-n-C10H21O | 1 | A3 | O | 10 | PO(OH)2 | |
| 319 | 4-n-C10H21O | 1 | A3 | O | 12 | PO(OH)2 | |
| 320 | 4-n-C10H21O | 1 | A4 | O | 3 | Si(OMe)3 | |
| 321 | 4-n-C10H21O | 1 | A4 | O | 4 | Si(OMe)3 | |
| 322 | 4-n-C10H21O | 1 | A4 | O | 4 | Si(OEt)3 | |
| 323 | 4-n-C10H21O | 1 | A4 | O | 4 | SiCl3 | |
| 324 | 4-n-C10H21O | 1 | A4 | O | 4 | PO(OH)2 | |

TABLE 1-continued

| | | | | | | | |
|---|---|---|---|---|---|---|---|
| 325 | 4-n-C10H21O | 1 | A4 | O | 10 | Si(OMe)3 | |
| 326 | 4-n-C10H21O | 1 | A4 | O | 10 | Si(OEt)3 | |
| 327 | 4-n-C10H21O | 1 | A4 | O | 10 | SiCl3 | |
| 328 | 4-n-C10H21O | 1 | A4 | O | 10 | PO(OH)2 | |
| 329 | 4-n-C10H21O | 1 | A4 | O | 12 | PO(OH)2 | |
| 330 | 3,4-(MeO)2 | 1 | A1 | O | 3 | Si(OMe)3 | |
| 331 | 3,4-(MeO)2 | 1 | A1 | O | 4 | Si(OMe)3 | |
| 332 | 3,4-(MeO)2 | 1 | A1 | O | 4 | Si(OEt)3 | |
| 333 | 3,4-(MeO)2 | 1 | A1 | O | 4 | SiCl3 | |
| 334 | 3,4-(MeO)2 | 1 | A1 | O | 4 | PO(OH)2 | |
| 335 | 3,4-(MeO)2 | 1 | A1 | O | 10 | Si(OMe)3 | |
| 336 | 3,4-(MeO)2 | 1 | A1 | O | 10 | Si(OEt)3 | [113-115° C.] |
| 337 | 3,4-(MeO)2 | 1 | A1 | O | 10 | SiCl3 | |
| 338 | 3,4-(MeO)2 | 1 | A1 | O | 10 | PO(OH)2 | |
| 339 | 3,4-(MeO)2 | 1 | A1 | O | 12 | PO(OH)2 | |
| 340 | 3,4-(MeO)2 | 1 | A2 | O | 3 | Si(OMe)3 | |
| 341 | 3,4-(MeO)2 | 1 | A2 | O | 4 | Si(OMe)3 | |
| 342 | 3,4-(MeO)2 | 1 | A2 | O | 4 | Si(OEt)3 | |
| 343 | 3,4-(MeO)2 | 1 | A2 | O | 4 | SiCl3 | |
| 344 | 3,4-(MeO)2 | 1 | A2 | O | 4 | PO(OH)2 | |
| 345 | 3,4-(MeO)2 | 1 | A2 | O | 10 | Si(OMe)3 | |
| 346 | 3,4-(MeO)2 | 1 | A2 | O | 10 | Si(OEt)3 | |
| 347 | 3,4-(MeO)2 | 1 | A2 | O | 10 | SiCl3 | |
| 348 | 3,4-(MeO)2 | 1 | A2 | O | 10 | PO(OH)2 | |
| 349 | 3,4-(MeO)2 | 1 | A2 | O | 12 | PO(OH)2 | |
| 350 | 3,4-(MeO)2 | 1 | A3 | O | 3 | Si(OMe)3 | |
| 351 | 3,4-(MeO)2 | 1 | A3 | O | 4 | Si(OMe)3 | |
| 352 | 3,4-(MeO)2 | 1 | A3 | O | 4 | Si(OEt)3 | |
| 353 | 3,4-(MeO)2 | 1 | A3 | O | 4 | SiCl3 | |
| 354 | 3,4-(MeO)2 | 1 | A3 | O | 4 | PO(OH)2 | |
| 355 | 3,4-(MeO)2 | 1 | A3 | O | 10 | Si(OMe)3 | |
| 356 | 3,4-(MeO)2 | 1 | A3 | O | 10 | Si(OEt)3 | |
| 357 | 3,4-(MeO)2 | 1 | A3 | O | 10 | SiCl3 | |
| 358 | 3,4-(MeO)2 | 1 | A3 | O | 10 | PO(OH)2 | |
| 359 | 3,4-(MeO)2 | 1 | A3 | O | 12 | PO(OH)2 | |
| 360 | 3,4-(MeO)2 | 1 | A4 | O | 3 | Si(OMe)3 | |
| 361 | 3,4-(MeO)2 | 1 | A4 | O | 4 | Si(OMe)3 | |
| 362 | 3,4-(MeO)2 | 1 | A4 | O | 4 | Si(OEt)3 | |
| 363 | 3,4-(MeO)2 | 1 | A4 | O | 4 | SiCl3 | |
| 364 | 3,4-(MeO)2 | 1 | A4 | O | 4 | PO(OH)2 | |
| 365 | 3,4-(MeO)2 | 1 | A4 | O | 10 | Si(OMe)3 | |
| 366 | 3,4-(MeO)2 | 1 | A4 | O | 10 | Si(OEt)3 | |
| 367 | 3,4-(MeO)2 | 1 | A4 | O | 10 | SiCl3 | |
| 368 | 3,4-(MeO)2 | 1 | A4 | O | 10 | PO(OH)2 | |
| 369 | 3,4-(MeO)2 | 1 | A4 | O | 12 | PO(OH)2 | |
| 370 | 4-C8F17-(CH2)2O | 1 | A1 | O | 3 | Si(OMe)3 | |
| 371 | 4-C8F17-(CH2)2O | 1 | A1 | O | 4 | Si(OMe)3 | |
| 372 | 4-C8F17-(CH2)2O | 1 | A1 | O | 4 | Si(OEt)3 | |
| 373 | 4-C8F17-(CH2)2O | 1 | A1 | O | 4 | SiCl3 | |
| 374 | 4-C8F17-(CH2)2O | 1 | A1 | O | 4 | PO(OH)2 | |
| 375 | 4-C8F17-(CH2)2O | 1 | A1 | O | 10 | Si(OMe)3 | |
| 376 | 4-C8F17-(CH2)2O | 1 | A1 | O | 10 | Si(OEt)3 | |
| 377 | 4-C8F17-(CH2)2O | 1 | A1 | O | 10 | SiCl3 | |
| 378 | 4-C8F17-(CH2)2O | 1 | A1 | O | 10 | PO(OH)2 | |
| 379 | 4-C8F17-(CH2)2O | 1 | A1 | O | 12 | PO(OH)2 | |
| 380 | 4-C8F17-(CH2)2O | 1 | A4 | O | 3 | Si(OMe)3 | |
| 381 | 4-C8F17-(CH2)2O | 1 | A4 | O | 4 | Si(OMe)3 | |
| 382 | 4-C8F17-(CH2)2O | 1 | A4 | O | 4 | Si(OEt)3 | |
| 383 | 4-C8F17-(CH2)2O | 1 | A4 | O | 4 | SiCl3 | |
| 384 | 4-C8F17-(CH2)2O | 1 | A4 | O | 4 | PO(OH)2 | |
| 385 | 4-C8F17-(CH2)2O | 1 | A4 | O | 10 | Si(OMe)3 | |
| 386 | 4-C8F17-(CH2)2O | 1 | A4 | O | 10 | Si(OEt)3 | |
| 387 | 4-C8F17-(CH2)2O | 1 | A4 | O | 10 | SiCl3 | |
| 388 | 4-C8F17-(CH2)2O | 1 | A4 | O | 10 | PO(OH)2 | |
| 389 | 4-C8F17-(CH2)2O | 1 | A4 | O | 12 | PO(OH)2 | |
| 390 | 4-C8F17-(CH2)2O | 1 | A2 | O | 3 | Si(OMe)3 | |
| 391 | 4-C8F17-(CH2)2O | 1 | A2 | O | 4 | Si(OMe)3 | |
| 392 | 4-C8F17-(CH2)2O | 1 | A2 | O | 4 | Si(OEt)3 | |
| 393 | 4-C8F17-(CH2)2O | 1 | A2 | O | 4 | SiCl3 | |
| 394 | 4-C8F17-(CH2)2O | 1 | A2 | O | 4 | PO(OH)2 | |
| 395 | 4-C8F17-(CH2)2O | 1 | A2 | O | 10 | Si(OMe)3 | |
| 396 | 4-C8F17-(CH2)2O | 1 | A2 | O | 10 | Si(OEt)3 | |
| 397 | 4-C8F17-(CH2)2O | 1 | A2 | O | 10 | SiCl3 | |
| 398 | 4-C8F17-(CH2)2O | 1 | A2 | O | 10 | PO(OH)2 | |
| 399 | 4-C8F17-(CH2)2O | 1 | A2 | O | 12 | PO(OH)2 | |
| 400 | 4-C8F17-(CH2)2O | 1 | A3 | O | 3 | Si(OMe)3 | |
| 401 | 4-C8F17-(CH2)2O | 1 | A3 | O | 4 | Si(OMe)3 | |
| 402 | 4-C8F17-(CH2)2O | 1 | A3 | O | 4 | Si(OEt)3 | |
| 403 | 4-C8F17-(CH2)2O | 1 | A3 | O | 4 | SiCl3 | |

TABLE 1-continued

| | | | | | | | |
|---|---|---|---|---|---|---|---|
| 404 | 4-C8F17-(CH2)2O | 1 | A3 | O | 4 | PO(OH)2 | |
| 405 | 4-C8F17-(CH2)2O | 1 | A3 | O | 10 | Si(OMe)3 | |
| 406 | 4-C8F17-(CH2)2O | 1 | A3 | O | 10 | Si(OEt)3 | |
| 407 | 4-C8F17-(CH2)2O | 1 | A3 | O | 10 | SiCl3 | |
| 408 | 4-C8F17-(CH2)2O | 1 | A3 | O | 10 | PO(OH)2 | |
| 409 | 4-C8F17-(CH2)2O | 1 | A3 | O | 12 | PO(OH)2 | |
| 410 | 2,3-Benzo | 1 | A1 | O | 3 | Si(OMe)3 | |
| 411 | 2,3-Benzo | 1 | A1 | O | 4 | Si(OMe)3 | |
| 412 | 2,3-Benzo | 1 | A1 | O | 4 | Si(OEt)3 | |
| 413 | 2,3-Benzo | 1 | A1 | O | 4 | SiCl3 | |
| 414 | 2,3-Benzo | 1 | A1 | O | 4 | PO(OH)2 | |
| 415 | 2,3-Benzo | 1 | A1 | O | 10 | Si(OMe)3 | |
| 416 | 2,3-Benzo | 1 | A1 | O | 10 | Si(OEt)3 | [112-113.5° C.] |
| 417 | 2,3-Benzo | 1 | A1 | O | 10 | SiCl3 | |
| 418 | 2,3-Benzo | 1 | A1 | O | 10 | PO(OH)2 | |
| 419 | 2,3-Benzo | 1 | A1 | O | 12 | PO(OH)2 | |
| 420 | 2,3-Benzo | 1 | A2 | O | 3 | Si(OMe)3 | |
| 421 | 2,3-Benzo | 1 | A2 | O | 4 | Si(OMe)3 | |
| 422 | 2,3-Benzo | 1 | A2 | O | 4 | Si(OEt)3 | |
| 423 | 2,3-Benzo | 1 | A2 | O | 4 | SiCl3 | |
| 424 | 2,3-Benzo | 1 | A2 | O | 4 | PO(OH)2 | |
| 425 | 2,3-Benzo | 1 | A2 | O | 10 | Si(OMe)3 | |
| 426 | 2,3-Benzo | 1 | A2 | O | 10 | Si(OEt)3 | |
| 427 | 2,3-Benzo | 1 | A2 | O | 10 | SiCl3 | |
| 428 | 2,3-Benzo | 1 | A2 | O | 10 | PO(OH)2 | |
| 429 | 2,3-Benzo | 1 | A2 | O | 12 | PO(OH)2 | |
| 430 | 2,3-Benzo | 1 | A3 | O | 3 | Si(OMe)3 | |
| 431 | 2,3-Benzo | 1 | A3 | O | 4 | Si(OMe)3 | |
| 432 | 2,3-Benzo | 1 | A3 | O | 4 | Si(OEt)3 | |
| 433 | 2,3-Benzo | 1 | A3 | O | 4 | SiCl3 | |
| 434 | 2,3-Benzo | 1 | A3 | O | 4 | PO(OH)2 | |
| 435 | 2,3-Benzo | 1 | A3 | O | 10 | Si(OMe)3 | |
| 436 | 2,3-Benzo | 1 | A3 | O | 10 | Si(OEt)3 | |
| 437 | 2,3-Benzo | 1 | A3 | O | 10 | SiCl3 | |
| 438 | 2,3-Benzo | 1 | A3 | O | 10 | PO(OH)2 | |
| 439 | 2,3-Benzo | 1 | A3 | O | 12 | PO(OH)2 | |
| 440 | 2,3-Benzo | 1 | A4 | O | 3 | Si(OMe)3 | |
| 441 | 2,3-Benzo | 1 | A4 | O | 4 | Si(OMe)3 | |
| 442 | 2,3-Benzo | 1 | A4 | O | 4 | Si(OEt)3 | |
| 443 | 2,3-Benzo | 1 | A4 | O | 4 | SiCl3 | |
| 444 | 2,3-Benzo | 1 | A4 | O | 4 | PO(OH)2 | |
| 445 | 2,3-Benzo | 1 | A4 | O | 10 | Si(OMe)3 | |
| 446 | 2,3-Benzo | 1 | A4 | O | 10 | Si(OEt)3 | |
| 447 | 2,3-Benzo | 1 | A4 | O | 10 | SiCl3 | |
| 448 | 2,3-Benzo | 1 | A4 | O | 10 | PO(OH)2 | |
| 449 | 2,3-Benzo | 1 | A4 | O | 12 | PO(OH)2 | |
| 450 | 4-CF3CO | 1 | A1 | O | 3 | Si(OMe)3 | |
| 451 | 3-CF3CO | 1 | A1 | O | 4 | Si(OMe)3 | |
| 452 | 3-CF3CO | 1 | A1 | O | 4 | Si(OEt)3 | |
| 453 | 3-CF3CO | 1 | A1 | O | 4 | SiCl3 | |
| 454 | 3-CF3CO | 1 | A1 | O | 4 | PO(OH)2 | |
| 455 | 3-CF3CO | 1 | A1 | O | 10 | Si(OMe)3 | |
| 456 | 3-CF3CO | 1 | A1 | O | 10 | Si(OEt)3 | |
| 457 | 3-CF3CO | 1 | A1 | O | 10 | Si(OMe)3 | |
| 458 | 3-CF3CO | 1 | A1 | O | 10 | PO(OH)2 | |
| 459 | 3-CF3CO | 1 | A1 | O | 12 | PO(OH)2 | |
| 460 | 3-CF3CO | 1 | A4 | O | 3 | Si(OMe)3 | |
| 461 | 3-CF3CO | 1 | A4 | O | 4 | Si(OMe)3 | |
| 462 | 3-CF3CO | 1 | A4 | O | 4 | Si(OEt)3 | |
| 463 | 3-CF3CO | 1 | A4 | O | 4 | SiCl3 | |
| 464 | 3-CF3CO | 1 | A4 | O | 4 | PO(OH)2 | |
| 465 | 3-CF3CO | 1 | A4 | O | 10 | Si(OMe)3 | |
| 466 | 3-CF3CO | 1 | A4 | O | 10 | Si(OEt)3 | |
| 467 | 3-CF3CO | 1 | A4 | O | 10 | SiCl3 | |
| 468 | 3-CF3CO | 1 | A4 | O | 10 | PO(OH)2 | |
| 469 | 3-CF3CO | 1 | A4 | O | 12 | PO(OH)2 | |
| 470 | 3-CF3CO | 1 | A2 | O | 3 | Si(OMe)3 | |
| 471 | 3-CF3CO | 1 | A2 | O | 4 | Si(OMe)3 | |
| 472 | 3-CF3CO | 1 | A2 | O | 4 | Si(OEt)3 | |
| 473 | 3-CF3CO | 1 | A2 | O | 4 | SiCl3 | |
| 474 | 3-CF3CO | 1 | A2 | O | 4 | PO(OH)2 | |
| 475 | 3-CF3CO | 1 | A2 | O | 10 | Si(OMe)3 | |
| 476 | 3-CF3CO | 1 | A2 | O | 10 | Si(OEt)3 | |
| 477 | 3-CF3CO | 1 | A2 | O | 10 | SiCl3 | |
| 478 | 3-CF3CO | 1 | A2 | O | 10 | PO(OH)2 | |
| 479 | 3-CF3CO | 1 | A2 | O | 12 | PO(OH)2 | |
| 480 | 3-CF3CO | 1 | A3 | O | 3 | Si(OMe)3 | |
| 481 | 3-CF3CO | 1 | A3 | O | 4 | Si(OMe)3 | |
| 482 | 3-CF3CO | 1 | A3 | O | 4 | Si(OEt)3 | |

TABLE 1-continued

| | | | | | | | |
|---|---|---|---|---|---|---|---|
| 483 | 3-CF3CO | 1 | A3 | O | 4 | SiCl3 | |
| 484 | 3-CF3CO | 1 | A3 | O | 4 | PO(OH)2 | |
| 485 | 3-CF3CO | 1 | A3 | O | 10 | Si(OMe)3 | |
| 486 | 3-CF3CO | 1 | A3 | O | 10 | Si(OEt)3 | |
| 487 | 3-CF3CO | 1 | A3 | O | 10 | SiCl3 | |
| 488 | 3-CF3CO | 1 | A3 | O | 10 | PO(OH)2 | |
| 489 | 3-CF3CO | 1 | A3 | O | 12 | PO(OH)2 | |
| 490 | 4-i-PrO | 0 | A1 | O | 3 | Si(OMe)3 | |
| 491 | 4-i-PrO | 0 | A1 | O | 4 | Si(OMe)3 | |
| 492 | 4-i-PrO | 0 | A1 | O | 4 | Si(OEt)3 | NMR* |
| 493 | 4-i-PrO | 0 | A1 | O | 4 | SiCl3 | |
| 494 | 4-i-PrO | 0 | A1 | O | 4 | PO(OH)2 | |
| 495 | 4-i-PrO | 0 | A1 | O | 10 | Si(OMe)3 | |
| 496 | 4-i-PrO | 0 | A1 | O | 10 | Si(OEt)3 | |
| 497 | 4-i-PrO | 0 | A1 | O | 10 | SiCl3 | |
| 498 | 4-i-PrO | 0 | A1 | O | 10 | PO(OH)2 | |
| 499 | 4-i-PrO | 0 | A1 | O | 12 | PO(OH)2 | |
| 500 | 4-t-BuO | 0 | A1 | O | 3 | Si(OMe)3 | |
| 501 | 4-t-BuO | 0 | A1 | O | 4 | Si(OMe)3 | |
| 502 | 4-t-BuO | 0 | A1 | O | 4 | Si(OEt)3 | NMR* |
| 503 | 4-t-BuO | 0 | A1 | O | 4 | SiCl3 | |
| 504 | 4-t-BuO | 0 | A1 | O | 4 | PO(OH)2 | |
| 505 | 4-t-BuO | 0 | A1 | O | 10 | Si(OMe)3 | |
| 506 | 4-t-BuO | 0 | A1 | O | 10 | Si(OEt)3 | |
| 507 | 4-t-BuO | 0 | A1 | O | 10 | SiCl3 | |
| 508 | 4-t-BuO | 0 | A1 | O | 10 | PO(OH)2 | |
| 509 | 4-t-BuO | 0 | A1 | O | 12 | PO(OH)2 | |
| 510 | 4-n-C10H21O | 0 | A1 | O | 3 | Si(OMe)3 | |
| 511 | 4-n-C10H21O | 0 | A1 | O | 4 | Si(OMe)3 | |
| 512 | 4-n-C10H21O | 0 | A1 | O | 4 | Si(OEt)3 | NMR* |
| 513 | 4-n-C10H21O | 0 | A1 | O | 4 | SiCl3 | |
| 514 | 4-n-C10H21O | 0 | A1 | O | 4 | PO(OH)2 | |
| 515 | 4-n-C10H21O | 0 | A1 | O | 10 | Si(OMe)3 | |
| 516 | 4-n-C10H21O | 0 | A1 | O | 10 | Si(OEt)3 | |
| 517 | 4-n-C10H21O | 0 | A1 | O | 10 | SiCl3 | |
| 518 | 4-n-C10H21O | 0 | A1 | O | 10 | PO(OH)2 | |
| 519 | 4-n-C10H21O | 0 | A1 | O | 12 | PO(OH)2 | |
| 520 | 4-C8F17-(CH2)2O | 0 | A1 | O | 3 | Si(OMe)3 | |
| 521 | 4-C8F17-(CH2)2O | 0 | A1 | O | 4 | Si(OMe)3 | |
| 522 | 4-C8F17-(CH2)2O | 0 | A1 | O | 4 | Si(OEt)3 | |
| 523 | 4-C8F17-(CH2)2O | 0 | A1 | O | 4 | SiCl3 | |
| 524 | 4-C8F17-(CH2)2O | 0 | A1 | O | 4 | PO(OH)2 | |
| 525 | 4-C8F17-(CH2)2O | 0 | A1 | O | 10 | Si(OMe)3 | |
| 526 | 4-C8F17-(CH2)2O | 0 | A1 | O | 10 | Si(OEt)3 | |
| 527 | 4-C8F17-(CH2)2O | 0 | A1 | O | 10 | SiCl3 | |
| 528 | 4-C8F17-(CH2)2O | 0 | A1 | O | 10 | PO(OH)2 | |
| 529 | 4-C8F17-(CH2)2O | 0 | A1 | O | 12 | PO(OH)2 | |

*$^1$H-NMR Data

| Compound No. (which is the same as that of Table 1) | Solvent/Chemical shift value ($\delta$ ppm, 270 MHz) |
|---|---|
| 2 | CDCl$_3$/0.71(t, 2H), 1.63(tt, 2H), 1.84(tt, 2H), 2.33(s, 3H), 3.58 (s, 9H), 4.00(t, 2H), 4.24(s, 2H), 6.87(d, 2H), 6.97(d, 2H), 7.08 (d, 2H), 7.52(d, 2H) |
| 3 | CDCl$_3$/0.70(t, 2H), 1.23(t, 9H), 1.63(tt, 2H), 1.85(tt, 2H), 2.33 (s, 3H), 3.85(q, 6H), 4.00(t, 2H), 4.24(s, 2H), 6.87(d, 2H), 6.97 (d, 2H), 7.07(d, 2H), 7.52(d, 2H) |
| 6 | CDCl$_3$/0.65(t, 2H), 1.3-1.6(br. 14H), 1.80(tt, 2H), 2.33(s, 3H), 3.57(s, 9H), 3.99(t, 2H), 4.24(s, 2H), 6.88(d, 2H), 6.97(d, 2H), 7.07(d, 2H), 7.52(d, 2H) |
| 7 | CDCl$_3$/0.63(t, 2H), 1.23(t, 9H), 1.3-1.6(br. 14H), 1.80(tt, 2H), 2.33(s, 3H), 3.82(q, 6H), 3.99(t, 2H), 4.24(s, 2H), 6.88(d, 2H), 6.97(d, 2H), 7.07(d, 2H), 7.52(d, 2H) |
| 9 | CDCl$_3$/7.52(d, J=9Hz, 2H), 7.07(d, J=8Hz, 2H), 6.97(d, J=8Hz, 2H), 6.88(d, J=9Hz, 2H), 4.24(s, 2H), 3.99(t, J=7Hz, 2H), 2.33 (s, 3H), 1.80(tt, J=7Hz, 2H), 1.51-1.23(m, 14H), 0.82(t, J=8Hz, 2H), 0.40(s, 6H) |
| 11 | DMSO-d$^6$/1.2-1.6(br. & m. 20H), 1.71(tt, 2H), 2.26(s, 3H), 4.04 (t, 2H), 4.53(s, 2H), 6.99(d, 2H), 7.08(q$_{AB}$, 4H), 7.57(d, 2H) |
| 12 | CDCl$_3$/1.2 to 1.8(br. & t. 28H), 2.33(s, 3H), 3.99(t, 2H), 4.09(dq, 4H), 4.24(s, 2H), 6.88(d, 2H), 6.97(d, 2H), 7.07(d, 2H), 7.57(d, 2H) |
| 43 | CDCl$_3$/0.70(t, 2H), 1.23(t, 9H), 1.64(tt, 2H), 1.86(tt, 2H), 3.85 (q, 6H), 4.01(t, 2H), 4.33(s, 2H), 6.90(d, 2H), 7.23(d, 2H), 7.54 (q$_{AB}$, 4H) |

TABLE 1-continued

| | |
|---|---|
| 47 | CDCl$_3$/0.67(t, 2H), 1.23(t, 9H), 1.53(br. 4H), 1.81(tt, 2H), 3.82 (q, 6H), 4.00(t, 2H), 4.33(s, 2H), 6.89(d, 2H), 7.23(d, 2H), 7.52 (d, 2H), 7.54(d, 2H) |
| 49 | CDCl$_3$/0.64(t, 2H), 1.2 to 1.5(br. 14H), 1.80(tt, 2H), 3.57(s, 9H), 4.00(t, 2H), 4.32(s, 2H), 6.90(d, 2H), 7.26(d, 2H), 7.53(2d, 4H) |
| 50 | CDCl$_3$/0.63(t, 2H), 1.23(t, 9H), 1.2 to 1.5(br. 14H), 1.80(tt, 2H), 3.82(q, 6H), 4.00(t, 2H), 4.32(s, 2H), 6.90(d, 2H), 7.24(d, 2H), 7.53(d, 2H), 7.54(d, 2H) |
| 54 | DMSO-d$^6$/1.2-1.8(br. &m. 22H), 4.05(t, 2H), 4.77(s, 2H), 7.09 (d, 2H), 7.38(d, 2H), 7.61(d, 2H), 7.69(d, 2H) |
| 55 | CDCl$_3$/1.2-1.8(br. 22H), 3.74(d, 6H), 4.00(t, 2H), 4.33(s, 2H), 6.90(d, 2H), 7.24(d, 2H), 7.53(d, 2H), 7.54(d, 2H) |
| 56 | CDCl$_3$/0.63(t, 2H), 1.26(t, 9H), 1.2 to 1.5(br. 40H), 1.82(tt, 2H), 3.84(q, 6H), 4.01(t, 2H), 4.33(s, 2H), 6.89(d, 2H), 7.23(d, 2H), 7.54(d, 2H), 7.55(d, 2H) |
| 169 | CDCl$_3$/0.69(t, 2H), 0.88(t, 3H), 1.21(t, 9H), 1.25(br., 14H), 1.60 (m, 4H), 1.83(m, 2H), 2.57(t, 2H), 3.83(q, 6H), 3.99(t, 2H), 4.24 (s, 2H), 6.86(d, 2H), 7.00(d, 2H), 7.05(d, 2H), 7.51(d, 2H) |
| 212 | CDCl$_3$/0.69(t, 2H), 0.88(t, 3H), 1.26(br, 20H), 1.42(m, 2H), 1.58 (tt, 2H), 1.81(tt, 2H), 2.57(t, 2H), 3.58(s, 9H), 3.99(t, 2H), 4.24 (s, 2H), 6.87(d, 2H), 7.00(d, 2H), 7.08(d, 2H), 7.51(d, 2H) |
| 213 | CDCl$_3$/0.65(t, 2H), 0.88(t, 3H), 1.2 to 1.4(br, 32H), 1.56(tt, 2H), 1.79(tt, 2H), 2.57(t, 2H), 3.57(s, 9H), 3.98(t, 2H), 4.24(s, 2H), 6.86(d, 2H), 6.99(d, 2H), 7.07(d, 2H), 7.50(d, 2H). |
| 214 | CDCl$_3$/0.63(t, 2H), 0.88(t, 3H), 1.23(t, 9H), 1.2 to 1.7(br. 34H), 1.79(tt, 2H), 2.57(t, 2H), 3.82(q, 6H), 3.98(t, 2H), 4.24(s, 2H), 6.86(d, 2H), 6.99(d, 2H), 7.07(d, 2H), 7.51(d, 2H). |
| 251 | CDCl$_3$/0.70(t, 2H), 1.25(t; J=6.7Hz, 9H), 1.62(tt; J=7.8Hz, 2H), 1.87(tt; J=7.8 HZ, 2H), 3.83(q; J=6.7Hz, 6H), 4.04(t; J=7.6Hz, 2H), 4.42(s, 2H), 6.97(d; J=9.3Hz, 2H), 7.70(d; J=9.3Hz, 2H). |
| 254 | CDCl$_3$/0.67(t, 2H), 1.23(t; J=6.7Hz, 9H), 1.5(m; 4H), 1.83(tt; J=7.8 HZ, 2H), 3.83(q; J=6.7Hz, 6H), 4.03(t; J=7.6Hz, 2H), 4.42(s, 2H), 6.97(d; J=9.3Hz, 2H), 7.70(d; J=9.3Hz, 2H). |
| 256 | CDCl$_3$/0.66(t, 2H), 1.24(t; J=6.7Hz, 9H), 1.2-1.6(br; 14H), 1.82(tt; J=7.8 HZ, 2H), 3.82(q; J=6.7Hz, 6H), 4.03(t; J=7.6Hz, 2H), 4.42(s, 2H), 6.97(d; J=9.3Hz, 2H), 7.70(d; J=9.3Hz, 2H). |
| 336 | CDCl$_3$/0.63(t, 2H), 1.23(t, 9H), 1.2 to 1.5(br. 14H), 1.79(tt, 2H), 3.75(s, 3H), 3.82(q, 6H), 3.86(s, 3H), 3.98(t, 2H), 4.22(s, 2H), 6.57(s, 1H), 6.62(d, 1H), 6.75(d, 1H), 6.89(d, 2H), 7.53(d, 2H) |
| 416 | CDCl$_3$/0.64(t, 2H), 1.23(t, 9H), 1.2 to 1.5(br. 14H), 1.76(tt, 2H), 3.81(q, 6H), 3.93(t, 2H), 4.79(s, 2H), 6.77(d, 2H), 7.22(d, 1H), 7.35(dd, 1H), 7.4 to 7.5(2d & 2dd, 4H), 7.82(d, 1H), 7.83(d, 2H). |
| 492 | CDCl$_3$/0.67(t, 2H), 1.22(t, J=7.0Hz, 9H), 1.33(d, J=5.9Hz, 6H), 1.58(tt like, 2H), 1.82(tt, J=7.0, 7.0Hz, 2H), 3.81(q, J=7.0Hz, 6H), 3.98(t, J=6.2Hz, 2H), 4.59(sep, J=5.9Hz, 1H), 6.94-6.88(m, 4H), 7.81-7.79(m, 4H). |
| 502 | CDCl$_3$/0.67(t, 2H), 1.22(t; J=7Hz, 9H), 1.25(m, 2H), 1.57(s, 9H), 1.83(m, 2H), 3.81(q; J=7Hz, 6H), 3.99(t; J=6.2Hz, 2H), 6.93 (d; J=8.9Hz, 2H), 7.02(d; J=8.9Hz, 2H), 7.80(d; J=8.9Hz, 2H), 7.84(d; J=8.9Hz, 2H). |
| 512 | CDCl$_3$/0.65(t, 2H), 0.88(t; J=6.7Hz, 3H), 1.2-1.6(t, br.s, m, 29H), 1.79(m. 4H), 3.81(q; J=6.8Hz, 6H), 3.95(t; J=6.7Hz, 2H), 3.97(t; J=6.7Hz, 2H), 6.92(d; J=8.9Hz, 2H), 7.82(d; J=8.9Hz, 2H). |

(Organic Thin Film Formed Body)

An organic thin film formed body according to the present invention is characterized by being prepared by forming an organic thin film by coating on a surface of a substrate a solution containing a compound represented by the aforementioned formula (1) (hereinafter, referred to as "compound (1)").

There are no particular limitations imposed on the substrate used, provided that it can allow formation of an organic thin film containing compound (1). Examples thereof include glass substrates such as a soda lime glass plate, and the like, substrates on which surface electrodes are formed, such as ITO glass and the like, substrates on which surface insulating or conductive layers are formed, silicon substrates such as silicon wafer substrates, and the like, ceramic substrates, and the like. It is preferable that the substrate be used after cleaning by using ozone; ultrasonic waves; distilled water, ion-exchanged water, detergent such as alcohols, or the like.

There are no particular limitations imposed on methods of forming an organic thin film containing compound (1) on the surface of the substrate. Examples thereof include a method by which a solution containing compound (1) is coated onto the substrate in accordance with a conventional coating method, followed by heating and drying the coated film. Examples of the coating method include coating methods using a conventional coating apparatus, such as a dipping method, a method using a spin coater, a method using a dye coater, a spraying method, and the like.

There are no particular limitations imposed on the solvents in which compound (1) is dissolved, provided that they are inert for compound (1) and can dissolve it. Examples thereof include aromatic hydrocarbons such as benzene, toluene, xylene, and the like; aliphatic hydrocarbons such as pentane, hexane, and the like; cycloaliphatic hydrocarbons such as cyclopentane, cyclohexane, and the like; esters such as methyl acetate, ethyl acetate, and the like; ethers such as diethylether, diisopropylether, 1,2-dimethoxyethane, THF, 1,4-dioxane, and the like; and ketones such as acetone, methylethylketone, methylisobutylketone, cyclohexanone, and the like.

After coating the film containing compound (1), it is preferably heated at 100 to 200° C. to remove the solvent to finish forming of the film. Moreover, it is preferable that solvent cleaning be carried out to remove organic molecular multilayers. Although there are no particular limitations imposed on the thickness of the produced organic thin film, it is usually approximately 1 to 100 nm.

The produced organic thin film has physical properties modified by light irradiation. For example, only an irradiated portion is changed to a hydrophilic thin film by ultraviolet irradiation. This change can be confirmed by, for example, measuring the change of contact angle against water. Thus, only the specific portion of a resist film which is prepared with a predetermined pattern after forming the organic thin film containing compound (1) on the substrate can be changed to a hydrophilic thin film by exposing the portion to ultraviolet light.

BEST MODE FOR CARRYING OUT THE INVENTION

In the following, the present invention will be explained in more detail. The present invention is not limited to the following examples. In the following examples, the compound numbers corresponds to those described in Table 1 shown above.

EXAMPLE 1

Synthesis of 4-(trifluoromethyl)benzyl-4-(4-(triethoxysilyl)butyloxy)phenylsulfone (Compound 43)

(a) Synthesis of 4-(4-trifluoromethylbenzyl sulfanyl)phenol 10 ml of methanol solution containing 2.8 g of 4-mercaptophenol was dropped with ice cooling into 20 ml of methanol solution containing 1.4 g of potassium hydroxide, followed by further stirring for 30 minutes. To this reaction mixture, 10 ml of methanol solution containing 5.0 g of 4-trifluoromethyl benzyl bromide was added with ice cooling, followed by stirring for 18 hours at room temperature. After concentrating the reaction mixture, ethyl acetate and water were added, followed by fractionating an organic layer. After the organic layer was dried with anhydrous magnesium sulfate, it was concentrated. The concentrate was purified by silica gel column chromatography (eluant: n-hexane/ethyl acetate/gradation) to produce 2.23 g of the desired product.

(b) Synthesis of 4-[(4-trifluoromethylphenyl)methanesulfonyl]phenol

To a 15 ml of acetic acid solution of 2.23 g of 4-(4-trifluoromethylbenzylsulfanyl)phenol was added slowly, 2.5 ml of 30% hydrogen peroxide solution at approximately 80° C. The reaction mixture was stirred for 3 hours at 90° C., then poured into water, and the resulted precipitate was collected by filteration. After washing with water, the precipitate was dried by heating under the reduced pressure to produce 2.34 g of the desired product.

(c) Synthesis of 4-(trifluoromethyl)benzyl-4-(3-butenyloxy)phenyl sulfone 2.34 g of 4-[(4-trifluoromethylphenyl)methanesulfonyl]phenol, 4.56 g of triphenylphosphine, and 0.80 g of 3-butene-1 ol were dissolved in 30 ml of dichloromethane, into which 5.56 g of 40% dichloromethane solution of azodicarboxylic acid diisopropyl ester was added with ice cooling. After the addition, the reaction mixture was warmed to room temperature, and was then stirred for 5 hours at room temperature. The reaction mixture was concentrated, and the concentrated material was purified by silica gel column chromatography (eluant: n-hexane/ethyl acetate=4/1 (volume ratio)) to produce 2.22 g of the desired product.

(d) Synthesis of 4-(trifluoromethyl)benzyl-4-(4-(triethoxysilyl)butyloxy)phenyl sulfone (Compound 43)

After 0.61 g of 4-(trifluoromethyl)benzyl-4-(3-butenyloxy)phenyl sulfone and 20 mg of 10% platinum-active carbon were charged in a reaction vessel, and the inside of the vessel was then filled with nitrogen gas, 2 ml of triethoxysilane was added, and the mixture was then further stirred at 100° C. for 4 hours. After the reaction mixture was cooled to room temperature, 20 ml of toluene was added, and the mixture was filtered through a pad of Celite™. After the filtrate was concentrated, dehydrated ethanol was added to the residue, which was then left still over night. After precipitated crystal was removed by filtration, the filtrate was concentrated, and n-hexane was added to collect precipitated crystal by filtration. The obtained crystal was washed with n-hexane to produce 0.53 g of the desired product.

Melting point: 124 to 128° C.

EXAMPLE 2

Synthesis of 4-methylbenzyl-4-(4-(triethoxysilyl)butyloxy)phenyl sulfone (Compound No. 3)

4-methylbenzylbromide was used as a starting material to produce a colorless oily material as the desired product in a manner similar to that of Example 1.

EXAMPLE 3

Synthesis of 4-methylbenzyl-4-(4-(trimethoxysilyl)butyloxy)phenyl sulfone (Compound No. 2)

The compound produced in Example 2 was refluxed with a chloroplatinic catalyst in methanol for 3 hours, and was then concentrated to give the desired product as a maize oily material.

EXAMPLE 4

Synthesis of 4-methylbenzyl-4-(12-(phosphono)dodecyloxy)phenyl sulfone (Compound No. 11)

After 50 ml of acetonitrile suspension containing 2.63 g of 4-[(4-methylphenyl)methanesulfonyl]phenol synthesized in a manner similar to that of Example 1 (a) and (b), 9.85 g of 1,12-dibromododecane, and 1.40 g of potassium carbonate were refluxed with heating for 4 hours, the mixture was concentrated, and was then fractionated with ethyl acetate and water. After the fractionated organic layer was dried and concentrated, the residue was recrystallized from hexane to give 3.73 g of 4-methylbenzyl-4-(12-bromododecyloxy)phenyl sulfone. 2.45 g of this compound and 20 mg of sodium iodide were refluxed with 10 ml of triethyl phosphite for 4 hours. The reaction mixture was poured into water, and extracted with ethyl acetate. After the obtained organic layer was dried and concentrated, the residue was recrystallized from hexane to give 2.15 g of 4-methylbenzyl-4-(12-(diethylphosphono)dodecyloxy)phenyl sulfone (compound 12).

After 2.5 g of this compound was further reacted in 20 ml of 30% hydrobromic acid acetic acid solution for 7 hours at 130° C., the mixture was poured into brine to precipitate crystal, which was filtered off, and washed with water, and was then dried well under reduced pressure at 80° C. to produce 2.12 g of the desired product.

Melting point: 148 to 150° C.

EXAMPLE 5

Synthesis of 4-isopropyloxyphenyl-4-(4-(triethoxysilyl)butyloxy)phenyl sulfone (Compound 492)

Triethoxysilane (3.0 ml, 2.63 g, 16 mmol) was added to a mixture of 4-isopropyloxy-4'-(3-butenyloxy)biphenyl sulfone (1.21 g, 3.5 mmol) synthesized from 4-isopropyloxy-4'-hydroxybiphenyl sulfone and 3-butenol in a manner similar to that of Example 3 and 10 wt % of Pt—C (50 mg), and the mixture was then stirred under nitrogen at 100° C. for 3 hours. After the mixture was concentrated under reduced pressure, the residue was diluted with toluene (20 ml) and the mixture was filtered through a pad of Celite™ to remove Pt catalyst. The filtrate was concentrated, and was then dried under reduced pressure to give the desired product (light brown oily material, 1.74 g).

EXAMPLE 6

Formation of an Organic Thin Film

An organig thin film was prepared from the solutions of compounds Nos. 2, 3, and 43. A representative method is as follows. The compound was diluted with anhydrous toluene as its concentration was 0.5% by weight in each case. A substrate, namely soda lime glass or silicon wafer which was pre-cleaned as cited below, was immersed into above solution for 10 minutes, and baked at 150° C. for 10 minutes. Then its surface was washed by immersing it in toluene with ultrasonic irradiation to remove over-layered adsorbed ingredients, and the resulted substrate was dried at 60° C. for 10 minutes to give an organic thin film of the compound.

Pre-Cleaning of Substrates

The substrate was washed with detergent with ultrasonic irradiation, with ion-exchanged water, and with ethanol, followed by drying at 60° C. then treated with UV/O3 cleaner before immersion.

EXAMPLE 7

Measurement of Contact Angle Change of the Organic Thin Film Influenced by Photo-Irradiation The contact angle was measured by using a contact angle measuring instrument (Type 360S manufactured by ERMA INC.) 60 seconds after 5 μl of water was dropped from a microsyringe onto each of the surfaces of the organic thin films formed on the soda lime glass according to the method described in Example 6. After each of the organic thin films was irradiated to light at 254 nm (bactericidal lamp, 2 mW/cm²) for a certain period of time, the contact angle thereof was measured. The compounds used and the changes over exposure time are shown in Table 2.

TABLE 2

| Compound No. | 0 (Initial value) | Past 10 minutes | Past 30 minutes | Past 60 minutes |
|---|---|---|---|---|
| 2 | 79.1 | — | — | 49.9 |
| 3 | 78.5 | — | — | 49.5 |

TABLE 2-continued

| Compound No. | 0 (Initial value) | Past 10 minutes | Past 30 minutes | Past 60 minutes |
|---|---|---|---|---|
| 43 | 86.3 | 67.7 | 47 | 47.2 |

It is apparent from Table 2 that each of the compounds according to the present invention (compounds nos. 2, 3, and 43) had its contact angle against water lowered to gain hydrophilicity over time past by ultraviolet irradiation.

INDUSTRIAL APPLICABILITY

According to the present invention, compound (1) which is flexibly amenable to the alteration of its structural part which affects film forming abilities and the resulting surface properties without impairing its photosensitivity, compound (1) being capable of undergoing surface alteration by irradiation with relatively low energy wavelength, and of forming an organic thin film on a substrate with good reproducibility, and the organic thin film formed body prepared by forming on a substrate an organic thin film containing compound (1) according to the present invention are provided.

The organic thin film containing compound (1) has a property that it is amenable to the alteration of its film physical properties by photo-irradiation. For example, only moiety exposed to ultraviolet rays can be converted to be hydrophilic, and so it is possible for an organic thin film on a substrate containing compound (1) according to the present invention to convert only a particular moiety to a hydrophilic thin film by ultraviolet irradiation through a predetermined pattern. According to the present invention, a fine and minute functional thin film pattern can be easily formed on the surface of a substrate.

The invention claimed is:

1. A compound represented by a formula (1)

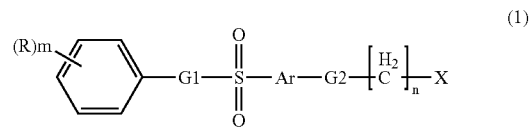

wherein X represents a silyl group which has a chlorine atom and may have a substituent, a silyl group which has a C1 to C4 alkoxy group and may have a substituent, a mercapto group, a C1 to C4 alkylthio group which may have a substituent, a C1 to C10 acylthio group, a disulfide group, or a phosphono group which may have a substituent, R represents a C1 to C20 alkyl group which may have a substituent, a C1 to C20 alkoxy group which may have a substituent an aryl group which may have a substituent, a C1 to C20 alkoxycarbonyl group which may have a substituent, or a halogen atom, R may form a ring with another R, n represents an integer of 1 to 30, m represents an integer of 0 to 5, R may be identical to, or may be different from each other, when m represents 2 or more, G1 represents a single bond or a bivalent saturated or unsaturated hydrocarbon radical having carbon atoms of 1 to 3, Ar represents an aromatic group which may have a substituent, G2 represents O, S or Nr, and r represents a hydrogen atom or a C1 to C4 alkyl group.

2. A compound according to claim 1, wherein Ar represents a para-phenylene group which may have a substituent, a para-biphenylene group which may have a substituent, a para-triphenylene group which may have a substituent, or a naphthylene group which may have a substituent.

3. A compound according to claim 1, wherein R represents a fluorine atom, a C1 to C20 alkyl group, a C1 to C20 fluoroalkyl group, a C1 to C20 alkoxy group, a C1 to C20 fluoroalkoxy group, or an aryl group.

4. An organic thin film formed body prepared by forming an organic thin film by coating onto a surface of a substrate a solution containing a compound represented by formula (1)

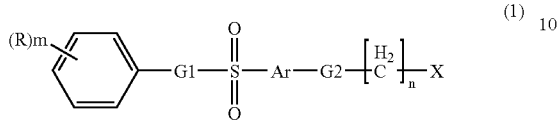

(1)

wherein X represents a heteroatom-containing functional group capable of interacting with a surface of a metal or a metallic oxide, R represents a C1 to C20 alkyl group which may have a substituent, a C1 to C20 alkoxy group which may have a substitutent an aryl group which may have a substituent, a C 1 to C20 alkoxycarbonyl group which may have a substituent, or a halogen atom, R may form a ring with another R, n represents an integer of 1 to 30, m represents an integer of 0 to 5, R may be identical to, or may be different from each other, when m represents 2 or more, G2 represents a single bond or a bivalent saturated or unsaturated hydrocarbon radical having carbon atoms of 1 to 3, Ar represents an aromatic group which may have a substituent, G2 represents O, S or Nr, and r represents a hydrogen atom or a C1 to C4 alkyl group.

* * * * *